United States Patent
Pilla et al.

(10) Patent No.: US 7,896,797 B2
(45) Date of Patent: Mar. 1, 2011

(54) ELECTROMAGNETIC FIELD TREATMENT APPARATUS AND METHOD FOR USING SAME

(75) Inventors: Arthur A. Pilla, Oakland, NJ (US); Andre' DiMino, Woodcliff Lake, NJ (US); David J. Muehsam, Cambridge, NY (US)

(73) Assignee: Ivivi Health Sciences, LLC, San Francisco, CA (US)

( * ) Notice: Subject to any disclaimer, the term of this patent is extended or adjusted under 35 U.S.C. 154(b) by 0 days.

(21) Appl. No.: 12/082,944

(22) Filed: Apr. 14, 2008

(65) Prior Publication Data
US 2009/0069626 A1   Mar. 12, 2009

Related U.S. Application Data

(60) Provisional application No. 60/922,894, filed on Apr. 12, 2007.

(51) Int. Cl.
*A61N 1/00* (2006.01)
(52) U.S. Cl. .......................................................... 600/13
(58) Field of Classification Search ................. 600/9–15; 128/897–899
See application file for complete search history.

(56) References Cited

U.S. PATENT DOCUMENTS

| | | | | |
|---|---|---|---|---|
| 3,890,953 A | * | 6/1975 | Kraus et al. | 600/14 |
| 4,105,017 A | * | 8/1978 | Ryaby et al. | 600/14 |
| 5,723,001 A | * | 3/1998 | Pilla et al. | 607/68 |
| 2005/0215842 A1 | * | 9/2005 | Pilla et al. | 600/9 |

* cited by examiner

*Primary Examiner* — Charles A Marmor, II
*Assistant Examiner* — Christine D Hopkins
(74) *Attorney, Agent, or Firm* — Shay Glenn LLP

(57) ABSTRACT

Larmor Precession makes specific predictions about bound ion dynamics, based upon specific combinations of AC and DC magnetic fields. Especially significant is the fact that the external magnetic field environment determines the overall qualities of resonances or particular changes in bio-effects. Given a target with a particular gyromagnetic ratio, Larmor Precession makes predictions that are determined solely by a magnetic field environment itself. An embodiment according to the present invention comprises specific combinations of AC and DC magnetic fields configured to produce specific bio-effects. Preferably an embodiment according to the present invention comprises using Larmor Precession to develop Electromagnetic Field environments targeted towards enhancing or diminishing specific biological processes, including tumor growth, bone and tissue repair, and biological processes and using Larmor Precession to generate magnetic field conditions that take advantage of specific behaviors, including resonances conditions.

22 Claims, 23 Drawing Sheets

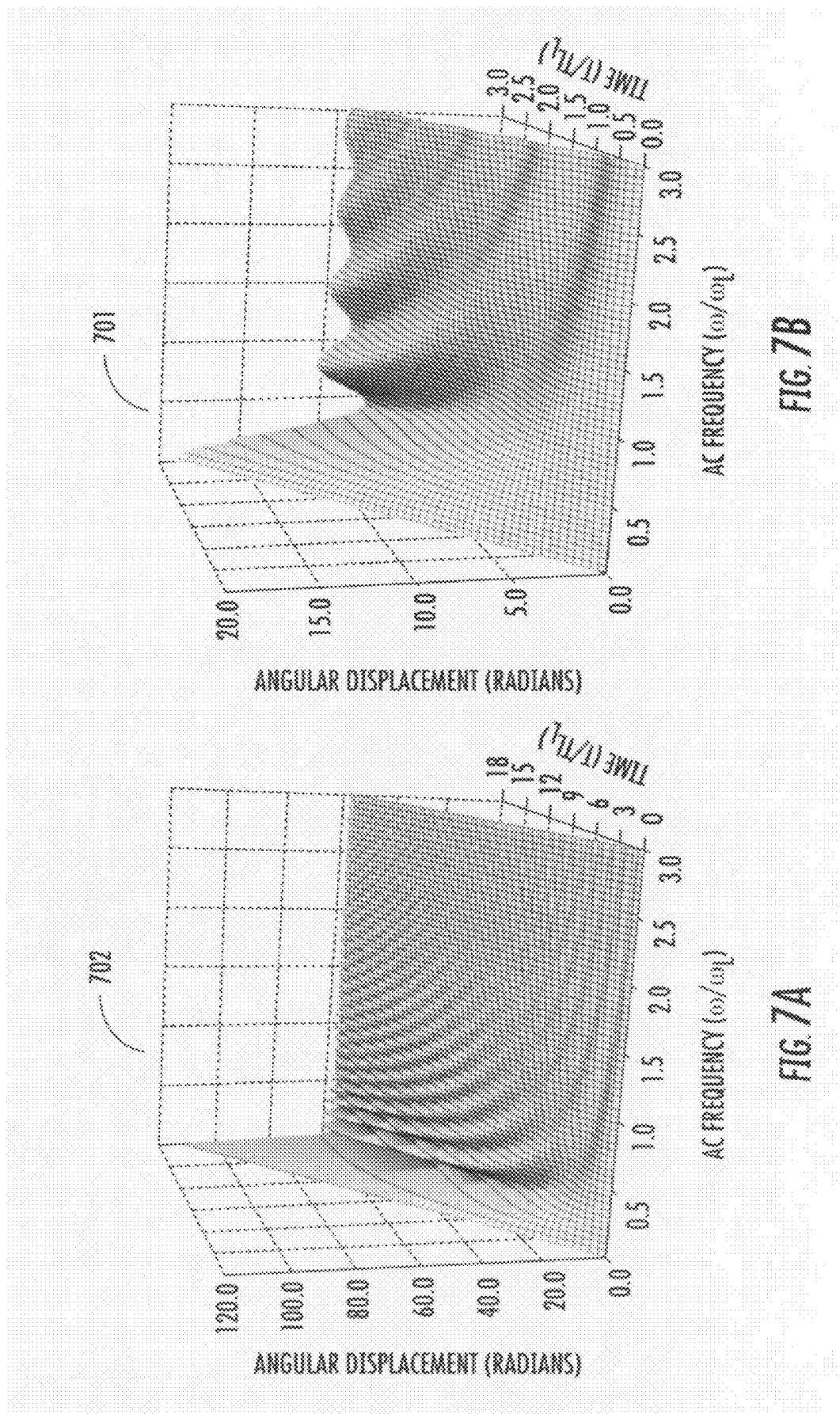

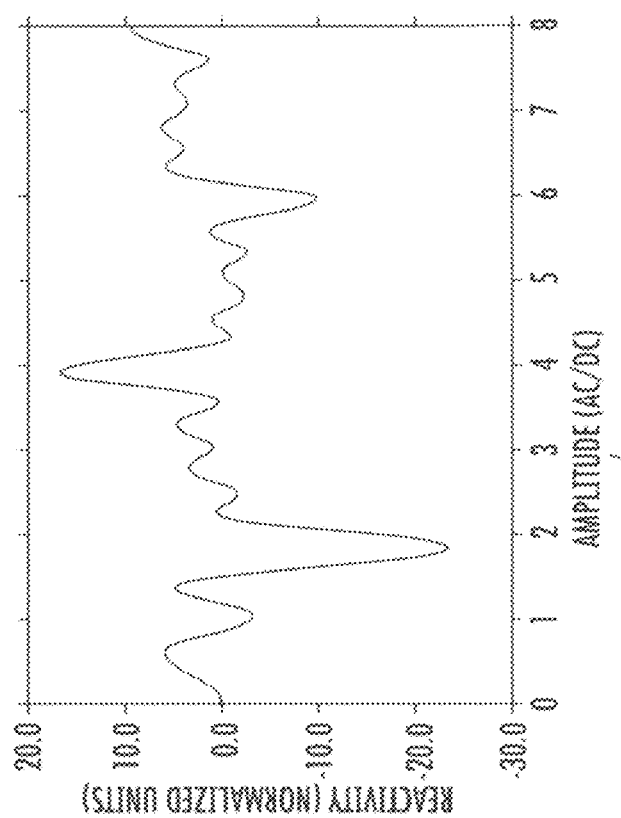
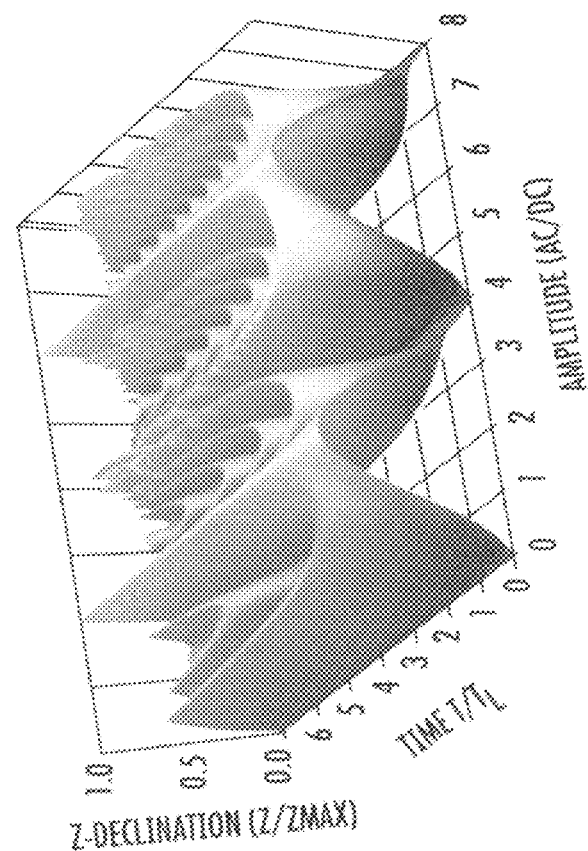

ELECTROMAGNETIC FIELD TREATMENT APPARATUS AND METHOD FOR USING SAME

This application claims the benefit of U.S. Provisional Application 60/922,894 filed Apr. 12, 2007, herein incorporated by reference in its entirety.

BACKGROUND OF THE INVENTION

1. Field of the Invention

This invention pertains generally to an apparatus and a method for therapeutically and prophylactically treating humans, animals and plants using static ("DC") and time-varying ("AC") magnetic fields ("MF") that are selected by optimizing amplitude and waveform characteristics of a time-varying electromagnetic field ("EMF") at target pathway structures such as molecules, cells, tissues and organs. An embodiment according to the present invention spatiotemporally configures MF to satisfy Larmor Precession conditions at the target pathway structure so that treatment can be provided for tissue growth and repair of humans, animals and plants. A method for configuring bio-effective EMF signals is provided, based upon the precise knowledge given by LP conditions of the effect of EMF upon a biological target. This knowledge is used to produce specific bio-response in the target. The method of construction of devices based upon LP conditions is given, including devices which directly employ the ambient EMF, including the geomagnetic field, as an integral component of the LP configured bio-effective field.

2. Discussion of Related Art

An important class of bio-effective EMF's exists including those due to static magnets having an amplitude and frequency of MF that are clearly too small to result in significant induced electric field ("IEF") effects. The observed bio-effects and therapeutic efficacy of these EMFs must thus be due directly to the MF. It is suggested that specific combinations of DC and low-frequency AC MFs may be configured to enhance or reduce specific biological processes.

DC and AC magnetic fields in the 1 Gauss ("G") to 4,000 G range have been reported to have significant therapeutic benefits for treatment of pain and edema from musculoskeletal injuries and pathologies. At the molecular level ambient range fields less than 1 G accelerated phosphorylation of a muscle contractile protein in a cell-free enzyme assay mixture. Fields ranging from 23 G to 3,500 G have been reported to alter the electrical properties of solutions as well as there physiological effects. At the cell level, a 300 G field doubled alkaline phosphatase activity in osteoblast-like cells. Fields in between 4,300 G and 4,800 G significantly increased turnover rate and synthesis of fibroblasts but had no effect on osteoblasts. Neurite outgrowth from embryonic chick ganglia was significantly increased by using fields in the range of 225 G and 900 G. Rat tendon fibroblasts exposed to 2.5 G showed extensive detachment of pre-attached cells, as well as temporarily altered morphology. A minimum MF gradient of 15 G/mm was required to cause 80% action potential blockade in an isolated nerve preparation. A series of studies demonstrated 10 G fields could significantly affect cutaneous microcirculation in a rabbit model. One of those studies showed a biphasic response dependent upon the pharmacologically determined state of a target.

Several double blind clinical studies using static magnets have been performed. A single 45 minute treatment using 300 G to 500 G fields reduced pain in post-polio patients by 76%. The magnets were placed on pain pressure points and not directly on a pain site. Discoloration, edema and pain were reduced by 40% up to 70% over a 7 day period post suction lipectomy. Pads containing arrays of 150 G to 400 G ceramic magnets were placed over a liposuction site immediately post-operative and remained over the site for 14 days. The outcome measures of fibromyalgia (pain, sleep disorders, etc.) were reduced by approximately 40% in patients who slept on a mattress pad containing arrays of 800 G ceramic magnets over a 4 month period. 90% of patients with diabetic peripheral neuropathy-received significant relief of pain, numbness and tingling using 475 G alternating pole magnetic insoles in a randomized, placebo-controlled crossover foot study. Only 30% of non-diabetic subjects showed equivalent improvement. Chronic lower back pain was not affected by application of a pad over the lumbar region having a geometric array of alternating pole 300 G fields for 6 hours/day, 3 times per week for one week.

The proven therapeutic efficacy of static MF devices and the wide range of bio-effects for low-frequency AC devices has resulted in the development of several models to explain the phenomena. Early observations of DC and AC magnetic field effects on calcium efflux and binding processes stimulated research into ion and ligand binding as the primary transduction pathway for a variety of observed effects. Early observations of amplitude windows and a dependence upon specific frequency and amplitude characteristics of DC and AC fields prompted the development of models predicting resonance conditions for particular combinations of fields. The ion cyclotron resonance ("ICR") model shows that magnetic fields act directly on the classical trajectory of a charged ion or ligand. However that model has been said to be physically unrealistic based on the grounds that cyclotron motion could not occur in a viscous medium and that the diameter of the cyclotron orbit at observed field strength would be much larger than the total size of the biological target itself.

Reports of amplitude windows for AC magnetic fields led to the development of quantum mechanical ion parametric resonance ("IPR") models that predict resonances. Those models appear to hold promise for predicting the location of resonances for combinations of AC and static magnetic fields. However one of the foremost objections to the predictive use of these models is that the numerical values produced depend critically upon factors such as the spherical symmetry of the Calcium ("Ca") binding site. Small perturbations from this symmetry will produce very large deviations from theoretical predictions. This suggests that apparent resemblance between experimental and theoretical resonances may be coincidental. Observed resonances have been suggested to also involve complex combinations of different target ions and the involvement of charged lipids on the surface of liposomes.

Models involving classical Lorentz force avoid the difficulties inherent in the ICR and IPR models.

Therefore, a need exists for an apparatus and a method that comprises controlling DC and ELF magnetic field effects by using a Larmor precession mechanism such that an effective acceleration, deceleration or inhibition of a number of physiological biochemical cascades, will occur.

SUMMARY OF THE INVENTION

The apparatus and method according to present invention, comprises delivering a pulsed electromagnetic field to human, animal and plant molecules, cells, tissues and organs for therapeutic and prophylactic purposes. Particularly an embodiment according to the present invention comprises the generation of any combination of AC and/or DC magnetic fields specifically configured to conform to LP conditions and resonances as described in detail below and the generation of any signal with AC and/or DC characteristics targeted towards the specific biochemical characteristics of a target.

Preferably an embodiment according to the present invention comprises modulation of any carrier EMF by any secondary signal or pattern designed to couple to a target by satisfying requirements of LP conditions, including but not limited to selection of specific numerical parameters employed in producing any specific waveform having specific characteristics targeted towards the specific biochemical characteristics of a target. The modulation through superposition, amplitude and frequency modulation, and the generation of effective envelopes using characteristic waveforms that satisfy LP conditions of a carrier waveform of varying or constant amplitude and frequency to form signals of known characteristics including waveform and power spectra tuned to dynamics and resonance frequencies of ion and ligand binding.

An embodiment according to the present invention comprises a method by which an ambient magnetic field, including the geomagnetic field, is detected to produce feedback which will allow spatial components of the geomagnetic field to be selectively enhanced, selectively reduced, or cancelled completely in order to configure a specific bio-effective magnetic field, based upon empirical evidence and/or a mathematical model.

An embodiment according to the present invention comprises a specific signal that is generated to satisfy LP conditions whereby a resulting composite MF signal is configured that can be applied to target pathway structures such as molecules, cells, tissues and organs for an exposure time of about 1 minute to about several hours per day, however other exposure times can be used.

Another embodiment according to the present invention comprises a MF modulated to satisfy LP conditions comprising any DC MF having an amplitude of 0.01 G to 5,000 G.

Another embodiment according to the present invention comprises a MF modulated to satisfy LP conditions comprising any AC MF having an amplitude of about 0.01 G to 5,000 G and a frequency from about 0.01 Hz to 36 MHz.

Another embodiment according to the present invention comprises a MF modulated to satisfy LP conditions comprising any DC or AC MF having an amplitude of about 0.01 G to 5,000 G in superposition with any AC or DC MF having an amplitude of about 0.01 G to 5,000 G and a frequency from about 0.01 Hz to 36 MHz for treatment of tissues, organs, cells and molecules.

Another embodiment according to the present invention comprises a MF modulated to satisfy LP conditions comprising any DC or AC MF having an amplitude of about 0.01 G to 5,000 G in superposition with any AC or DC MF having an amplitude of about 0.01 G to 5,000 G and a frequency from about 0.01 Hz to 36 MHz to enhance any biochemical process in tissues, organs, cells and molecules.

Another embodiment according to the present invention comprises a MF modulated to satisfy LP conditions comprising any DC or AC MF having an amplitude of about 0.01 G to 5,000 G in superposition with any AC or DC MF having an amplitude of about 0.01 G to 5,000 G and a frequency from about 0.01 Hz to 36 MHz to inhibit any biochemical process in tissues, organs, cells and molecules.

Another embodiment according to the present invention comprises superposition of any signal satisfying LP conditions with a bipolar pulse train of known characteristics yielding a signal of variable waveform with amplitude from about 0.01 G to 5,000 G to enhance or to inhibit any biochemical process in tissues, organs and cells.

Another embodiment according to the present invention comprises superposition of any signal satisfying LP conditions with a bipolar pulse train of known characteristics yielding a signal of variable waveform having an amplitude from about 0.01 G to 5,000 G for treatment of tissues, organs, cells or tissues.

Another embodiment according to the present invention comprises application of any carrier signal modulated to satisfy LP conditions using inductively coupled signal transmission equipment, electrodes implanted into or placed on a surface of a target, or any other method of applying the signal for treatment of tissues, organs, cells, and molecules.

Another embodiment according to the present invention comprises at least one flexible inductively coupled transmission coil that can be incorporated into anatomical wraps and supports for treatment of tissues, organs, cells and molecules.

Another embodiment according to the present invention comprises at least one flexible inductively coupled transmission coil that can be incorporated into bandages and dressings for treatment of tissues, organs, cells and molecules.

Another embodiment according to the present invention comprises at least one flexible inductively coupled transmission coil that can be incorporated into everyday garments and articles of clothing to allow for the within described treatment of tissues, organs, cells and molecules on an ambulatory basis.

Another embodiment according to the present invention comprises at least one flexible inductively coupled transmission coil that can be incorporated into beds, mattresses, pads, chairs, benches and any other structure designed to support an anatomical structure of a human and animal.

Another embodiment according to the present invention comprises employing a plurality of flexible inductively coupled transmission coils such that the coils provide increased coverage area for treatment of large areas of tissues, organs, cells and molecules.

Another embodiment according to the present invention comprises an apparatus that operates at reduced power levels than conventional electro-medical devices.

"About" for purposes of the invention means a variation of plus or minus 50%.

"Ambient Field" for purposes of this invention includes geomagnetic fields and fields generated by any devices that may be transmitted to the treatment site.

"Bio-effective" for purposes of the invention means biological and physiological outcomes of biochemical cascades related to augmenting or diminishing tissue growth and repair.

"LP resonances" for purposes of the invention means the computation of resonance conditions through any means that employs the dynamics of LP in order to compute resonance conditions.

The above and yet other aspects and advantages of the present invention will become apparent from the hereinafter set forth Brief Description of the Drawings and Detailed Description of the Invention.

BRIEF DESCRIPTION OF THE DRAWINGS

Methods and apparatus that are particular embodiments of the invention will now be described, by way of example, with reference to the accompanying diagrammatic drawings:

FIGS. 7A and 7B are graphs illustrating reactivity on binding lifetime for an AC/DC parallel magnetic field combination;

FIG. 10 illustrates on the left a sample declination of axis or precession from z-axis as a function of time and ratio of DC/AC amplitudes, and on the right the reactivity for perpendicular field configuration;

DETAILED DESCRIPTION OF THE INVENTION

Figure 1:
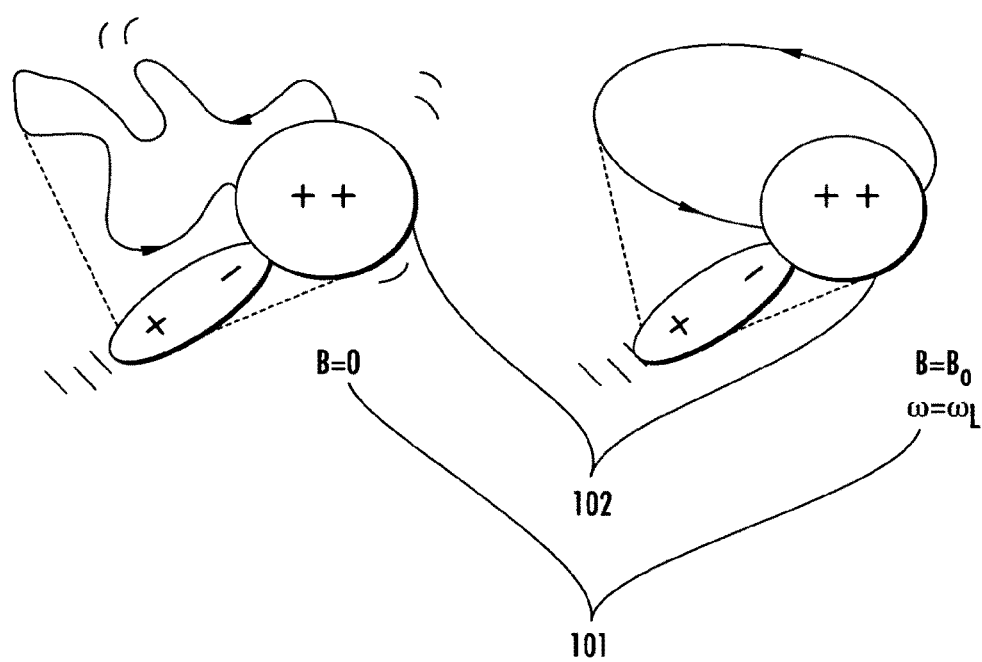
FIG. 1 illustrates an effect of a magnetic field on charged ion bound within a signaling molecule.

LP is a means by which a magnetic field introduces coherence into the motion of bound ions. Larmor's theorem states that for a magnetic moment, the introduction of a magnetic field results in the original motion transferred into a frame of reference rotating at Larmor frequency:

$$\omega_L = \Gamma B, \tag{1}$$

Where $\Gamma$ is a gyromagnetic ratio of a processing system. $\Gamma = q/2m$ where q is charge and m is mass for a target such as a single calcium ion.

Bound charges in a biological target will generally undergo thermally induced oscillations thus giving rise to a magnetic moment for a system. Such a system can be expected to undergo LP. This motion will persist in superposition with thermal forces until thermal forces eventually eject the oscillator from a binding site. For a magnetic field oriented along the z-axis, precessional motion will be confined to the x-y plane. In addition to coherent precessional motion of a bound oscillator, contributions to the motion due to thermal noise itself are also expected to undergo precession.

Larmor Precession is an effect of magnetic fields on magnetic moments that, while the underlying mechanism is quantum mechanical and involves a change in relative phases of the spin-up and spin-down components of a magnetic moment, can be described through a classical model. An illustrative classical model utilizes a Lorentz-Langevin equation for an ion bound in a potential well subject to a magnetic field oriented up along the z-axis is in the presence of thermal noise:

$$\frac{d^2 r}{dt^2} = -\beta \frac{dr}{dt} + \gamma \frac{dr}{dt} \times B_o k - \omega^2 r + n. \tag{2}$$

Where r is the position vector of a particle; $\beta$ is the viscous damping coefficient per unit mass due to molecular collisions in the thermal bath, $\gamma$ is the ion charge to mass ratio; $B_0$ is the magnitude of the magnetic field vector; k is the unit vector along the z-axis; $\omega$ is the angular frequency of the oscillator and n is the random thermal noise force per unit mass. Although the potential energy function shown here is that of the harmonic oscillator, the precession is not limited to the case of linear isotropic potential but is expected to occur for any central restorative potential.

Solution of the Lorentz equation in closed form is possible for special cases or through numerical integration. The addition of the thermal term n to the Lorentz equation produces a solution that can be assessed via statistical mechanical methods to produce the ensemble average <r(t)> for the ion position as a function of time. From the ensemble average, the effects on bound lifetime of thermal noise, exogenous magnetic fields and changes in physical parameters can be evaluated.

The solution of the Lorentz-Langevin equation is $$u(t) = c_1 e^{\lambda_1 t} + c_2 e^{\lambda_2 t} + \psi_n(t)$$

where $$u = x + iy; \ c_1 = -c_2 = \frac{-u_o'}{(\lambda_2 - \lambda_1)};$$
$$u(0) = 0, \ u'(0) = -u_o'; \ <|u_{0'}|^2> = \frac{2kT}{m}, \tag{3}$$

and $$\lambda_{1,2} = \frac{-\alpha \pm \sqrt{\alpha^2 - 4\omega^2}}{2}; \ \alpha = \beta + i B_o \gamma. \tag{4}$$

The ionic trajectory thus comprises a coherent part: $c(t) = c_1 e^{\lambda_1 t} + c_2 e^{\lambda_2 t}$, and a component due to thermal noise: $\psi_n(t)$, i.e. the particular solution to the non-homogeneous equation. The coherent component of the solution has been shown to be, for physically realistic values of parameters, a damped oscillation in the infrared range, undergoing precessional motion at the Larmor frequency about the axis of the magnetic field $$c(t) \approx \frac{u_{o'}}{i\omega} e^{-\frac{\beta}{2}t} e^{-i\omega_L t} \left[ \frac{e^{-i\omega t} - e^{i\omega t}}{2} \right] = \frac{-u_{o'}}{\omega} e^{-\frac{\beta}{2}t} e^{-i\omega_L t} \sin(\omega t). \tag{5}$$

The particular solution to the non-homogeneous equation including thermal noise is given by $$\psi_n(t) = \frac{1}{\lambda_2 - \lambda_1} \left[ e^{\lambda_2 t} \int_0^t e^{-\lambda_2 \tau} n(\tau) d\tau - e^{\lambda_1 t} \int_0^t e^{-\lambda_1 \tau} n(\tau) d\tau \right] \tag{6}$$

The rate of growth of the thermal term $\psi_n(t)$ has been assessed previously via the ensemble average of the oscillator amplitude, where it was shown the accumulation term grows with time, eventually overwhelming the attenuation of the oscillator trajectory due to viscous damping, $$e^{-\frac{\beta}{2}t}.$$

Thermal accumulation causes the oscillating ion to be ejected from the binding site after a bound lifetime dependent upon the thermal noise spectral density, $$\sigma_n^2 = \frac{2\beta kT}{m}.$$

It was also shown that binding lifetimes on the order of one second result for physically relevant values of the oscillator frequency ($\omega \approx 10^{12}$), viscous damping ($\beta \approx 1\text{-}10$), and magnetic field strength $B_0 \ll 1$ T.

The time-dependence of $\psi_n(t)$ may also be evaluated, expanding equation (6):

$$\psi_n(t) = \frac{1}{\lambda_2 - \lambda_1} \begin{bmatrix} e^{\frac{-\alpha - \sqrt{\alpha^2 - 4\omega^2}}{2}t} \int_0^t e^{-\lambda_2 \tau} n(\tau) d\tau - \\ e^{\frac{-\alpha + \sqrt{\alpha^2 - 4\omega^2}}{2}t} \int_0^t e^{-\lambda_1 \tau} n(\tau) d\tau \end{bmatrix}, \tag{7}$$

$$= \frac{1}{\lambda_2 - \lambda_1} e^{-\frac{\alpha}{2}t} \begin{bmatrix} e^{-\frac{\sqrt{\alpha^2 - 4\omega^2}}{2}t} \int_0^t e^{-\lambda_2 \tau} n(\tau) d\tau - \\ e^{\frac{\sqrt{\alpha^2 - 4\omega^2}}{2}t} \int_0^t e^{-\lambda_1 \tau} n(\tau) d\tau \end{bmatrix},$$

or $$\psi_n(t) = \frac{1}{\lambda_2 - \lambda_1} e^{-\frac{\beta}{2}t} e^{-\frac{i\omega_L}{2}t} [Y(t)]. \tag{8}$$

where $$[Y(t)] = \begin{bmatrix} e^{\frac{\sqrt{\alpha^2 - 4\omega^2}}{2}t} \int_0^t e^{-\lambda_2 \tau} n(\tau) d\tau - \\ e^{\frac{\sqrt{\alpha^2 - 4\omega^2}}{2}t} \int_0^t e^{-\lambda_1 \tau} n(\tau) d\tau \end{bmatrix} \tag{9}$$

is the accumulation of the thermal component with respect to time.

Thus, equation (7) shows that the thermal component of the oscillation itself also undergoes Larmor precession.

The specific rate of growth of the processing term may be found by assessing the physically relevant case:

$$|\alpha^2| \ll 4\omega^2, \ e^{\pm \frac{\sqrt{\alpha^2 - 4\omega^2}}{2}t} \to e^{\pm i\omega t},$$

so that:

$$\psi_n(t) = \frac{1}{\lambda_2 - \lambda_1} e^{-\frac{\beta}{2}t} e^{-\frac{iB_o \gamma}{2}t} \begin{bmatrix} e^{-i\omega t} \int_0^t e^{+\frac{\alpha}{2}\tau} e^{i\omega\tau} n(\tau) d\tau - \\ e^{i\omega t} \int_0^t e^{+\frac{\alpha}{2}\tau} e^{-i\omega\tau} n(\tau) d\tau \end{bmatrix} \tag{10}$$

$$= \frac{-1}{\lambda_2 - \lambda_1} e^{-\frac{\beta}{2}t} e^{-\frac{iB_o \gamma}{2}t} \begin{bmatrix} \int_0^t e^{+\frac{\alpha}{2}\tau} (e^{i\omega(t-\tau)} - e^{-i\omega(t-\tau)}) \\ n(\tau) d\tau \end{bmatrix}$$

$$= \frac{-2i}{\lambda_2 - \lambda_1} e^{-\frac{\beta}{2}t} e^{-\frac{iB_o \gamma}{2}t} \left[ \int_0^t e^{+\frac{\alpha}{2}\tau} \sin(\omega(t-\tau)) n(\tau) d\tau \right]. \tag{11}$$

Thus, the thermal component of the ion trajectory itself comprises a thermal oscillator driven by thermal noise $n(\tau)$, subject to viscous damping and undergoing precessional motion at the Larmor frequency about the axis defined by the magnetic field. Note that the exponentials in the integrand of equation (10) receive a + sign, due to the terms in $-\lambda_{1,2}$ in equation (10), in accord with the physical expectation that thermal noise acts to increase the oscillator amplitude.

The accumulation of $\psi_n(t)$ may be evaluated in a straight-forward manner via the ensemble average of the oscillator position. Assessing the thermal term, $u(t)=x+iy=\psi_n(t)$, it is convenient to retain the exponential terms in equation (10):

$$x^2 + y^2 = |\psi_n(t)|^2 \quad (12)$$

$$= \left| \frac{-1}{\lambda_2 - \lambda_1} e^{-\frac{\beta}{2}t} e^{-\frac{iB_o\gamma}{2}t} \left[ \int_0^t e^{+\frac{\alpha}{2}\tau} (e^{i\omega(t-\tau)} - e^{-i\omega(t-\tau)}) n(\tau) d\tau \right] \right|^2$$

$$= \frac{e^{-\beta t}}{|\lambda_2 - \lambda_1|^2} \left[ \int_0^t e^{+\frac{\alpha}{2}\tau} e^{+\frac{\alpha^*}{2}\tau} (e^{i\omega(t-\tau)} - e^{-i\omega(t-\tau)}) (e^{-i\omega(t-\tau)} - e^{i\omega(t-\tau)}) n(\tau) n^*(\tau) d\tau \right].$$

Employing the fact that viscosity and thermal noise spectral density $\sigma_n^2$ are related by $$\sigma_n^2 = \frac{2\beta kT}{m}$$

where k is the Boltzmann constant, T the absolute temperature, and m the mass of the particle, the ensemble average is, since $a+a^*=2\beta$, $$|\psi_n(t)|^2 = \frac{\sigma_n^2}{|\lambda_2 - \lambda_1|^2} e^{-\beta t} \left[ \int_0^t e^{+\beta\tau} (e^{i\omega(t-\tau)} - e^{-i\omega(t-\tau)}) (e^{-i\omega(t-\tau)} - e^{i\omega(t-\tau)}) d\tau \right] \quad (13)$$

or $$|\psi_n(t)|^2 = \frac{\sigma_n^2}{|\lambda_2 - \lambda_1|^2} e^{-\beta t} \left[ \int_0^t e^{+\beta\tau} (2 - e^{2i\omega(t-\tau)} - e^{-2i\omega(t-\tau)}) d\tau \right] \quad (14)$$

$$= \frac{\sigma_n^2}{|\lambda_2 - \lambda_1|^2} e^{-\beta t} \left[ \frac{2}{\beta}(e^{+\beta t} - 1) - \frac{e^{2i\omega t}}{\beta - 2i\omega} \right.$$
$$\left. (e^{(\beta-2i\omega)t} - 1) - \frac{e^{-2i\omega t}}{\beta + 2i\omega} (e^{(\beta+2i\omega)t} - 1) \right]$$

$$= \frac{\sigma_n^2}{|\lambda_2 - \lambda_1|^2} e^{-\beta t} [e^{+\beta t} - 1] \left( \frac{2}{\beta} - \frac{1}{\beta - 2i\omega} - \frac{1}{\beta + 2i\omega} \right),$$

or, $$|\psi_n(t)|^2 = \frac{\frac{2kT}{m}}{|\lambda_2 - \lambda_1|^2} \left( 1 - \frac{\beta^2}{\beta^2 + 4\omega^2} \right)(1 - e^{-\beta t}). \quad (15)$$

Thus, the thermal term $\psi_n(t)$ will increase in amplitude with time. Note that the time-dependence of the magnetic field contribution to the thermal accumulation disappears when $|\alpha^2| \ll 4\omega^2$. The more general case was described previously. FIG. 1 illustrates a schematic of effect of magnetic field 101 on the motion of a charged ion 102, such as calcium, bound inside a signaling molecule such as calmodulin or troponin C. It can be seen that the magnetic field introduces coherence into the ion trajectory within the binding site.

Figure 2:
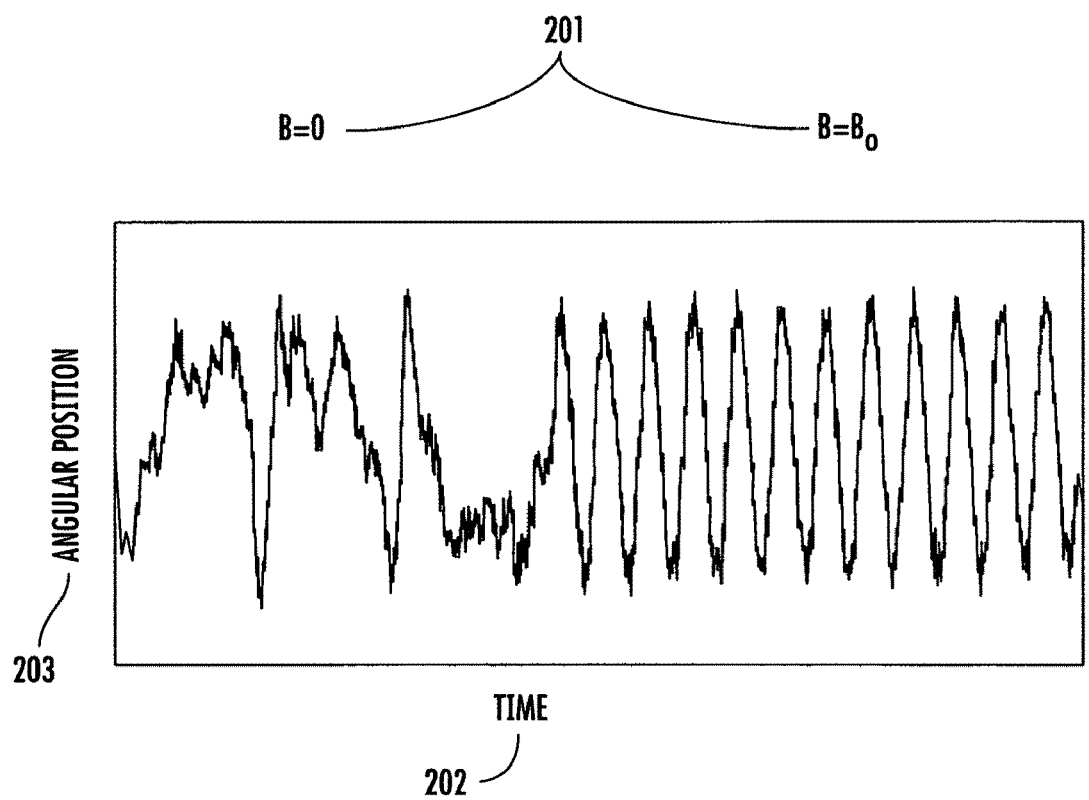
FIG. 2 depicts Larmor Precession of a bound ion wherein thermal noise and an applied magnetic field are present.

The thermal component of an ion trajectory comprises an harmonic oscillator driven by thermal noise $n(\tau)$, subject to viscous damping and undergoing precessional motion at the Larmor frequency about an axis defined by the magnetic field. FIG. 2 depicts angular position of a bound ion in the presence of thermal noise and an applied magnetic field 201, time 202, and angular position 203. This significant result applies to all such bound charged oscillators, indicating that the LP mechanism can be responsible to MF effects in a wide variety of target systems.

For physically relevant values of the oscillator frequency ($\omega \approx 10^{12}$), viscous damping ($\beta \approx 1\text{-}10$), and magnetic field strength $B_o \triangleleft 1$ Tesla, the results have been assessed via numerical simulation. It has been shown that the accumulation term grows with time, eventually overwhelming the attenuation of the oscillator trajectory due to viscous damping $$e^{-\frac{\beta}{2}t}.$$

Thermal accumulation thus causes the oscillating ion to be ejected from the binding site after a bound lifetime dependent upon the thermal noise spectral density.

Although thermal forces will in general be distributed throughout the spherical solid angle available in the binding site, it is important to bear in mind that the ion or ligand is not executing random motions in an isotropic region. Rather, it is strongly bound in an oscillator potential, with oscillator frequency in the infrared. Thus, the motion is that of a thermally driven oscillator rather than a random motion, as shown above, through examination of the accumulation term $\psi_n(t)$. Rather than simply rapidly ejecting an ion or ligand from a binding site, thermal noise forces will themselves contribute to the amplitude of the precessional component of the motion. Thus, both the coherent and the thermal parts of the total motion $u(t)=c(t)+\psi_n(t)$ will undergo LP. The implications of this is wide-ranging: an extensive variety of charged oscillators in the biological target system can be expected to undergo LP, resulting in a wide variety of target systems exhibiting similar responses to applied magnetic fields.

Larmor Precession conditions are described below according to an embodiment of the present invention.

For precessional motion of a bound oscillator to influence a biochemical process, it is clear that the motion must be able to move through a significant portion of one precessional orbit. Thus, the time constant of a target process must be on the order of a period of the LP in order for a bio-effect to occur. Weaker magnetic fields can only expected to target relatively slower biological process, and a lower limit for magnetic field effects can be established. For example, the Larmor frequency for Ca at 50 µT is approximately 18.19 Hz, so that a bound lifetime of about 55 msec is required for one orbit to occur. Ca binding to calmodulin ("CaM") has a maximal lifetime on the order of ≈1 sec, for the slow pair of binding sites on the CaM molecule, resulting in a lower limit of about 1-3 µT for detectability by CaCaM.

Precessional motion of the oscillator will result in a coherent modulation of the rate at which the oscillator moves through the available range of motion. Although the mechanisms by which this coherent motion can influence kinetics it will certainly vary from one target system to another, the basic properties of the Larmor model will be similar for a wide variety of systems. The rate at which the oscillator passes through various orientations, including preferred orientations that may influence kinetics, will be modulated coherently by the precessional motion at the Larmor frequency. This introduction of coherence into a process that, in the absence of magnetic fields, is governed by thermal perturbations, allows the magnetic field to impart information to the system without requiring substantial energetic input on the part of the field. It has been shown that the angular momentum of a calcium ion undergoing LP in a 50 µT magnetic field is on the order of Planck's constant.

Larmor precession results in the oscillator sweeping out an angular area within the binding site, at a rate determined by the gyromagnetic ratio of the target and the magnetic field.

For example, for CaCaM binding, LP will result in a modulation of the rate at which the oscillator makes contact with various portions of the binding site. Stronger magnetic fields will increase this rate, thus increasing the probability or frequency at which the oscillator contacts orientations that favor dissociation. Increasing MF strength thus results in a reduction of the bound lifetime of Ca, resulting in a greater availability of free Ca as observed for the increased reaction rates observed in a cell-free preparation.

For a system such as CaCaM, bio-effects are expected to increase with field strength, reaching a saturation level, beyond which further increases in DC field strength result in only small changes in binding time, relative to the initial kinetics of the system. The percentage change in reactivity, or binding lifetime, as compared to the zero-field lifetime is given by:

$$\Delta\% = 100 \frac{T_{B=0} - T_{B=B_o}}{T_{B=0}}. \tag{16}$$

Figure 3:
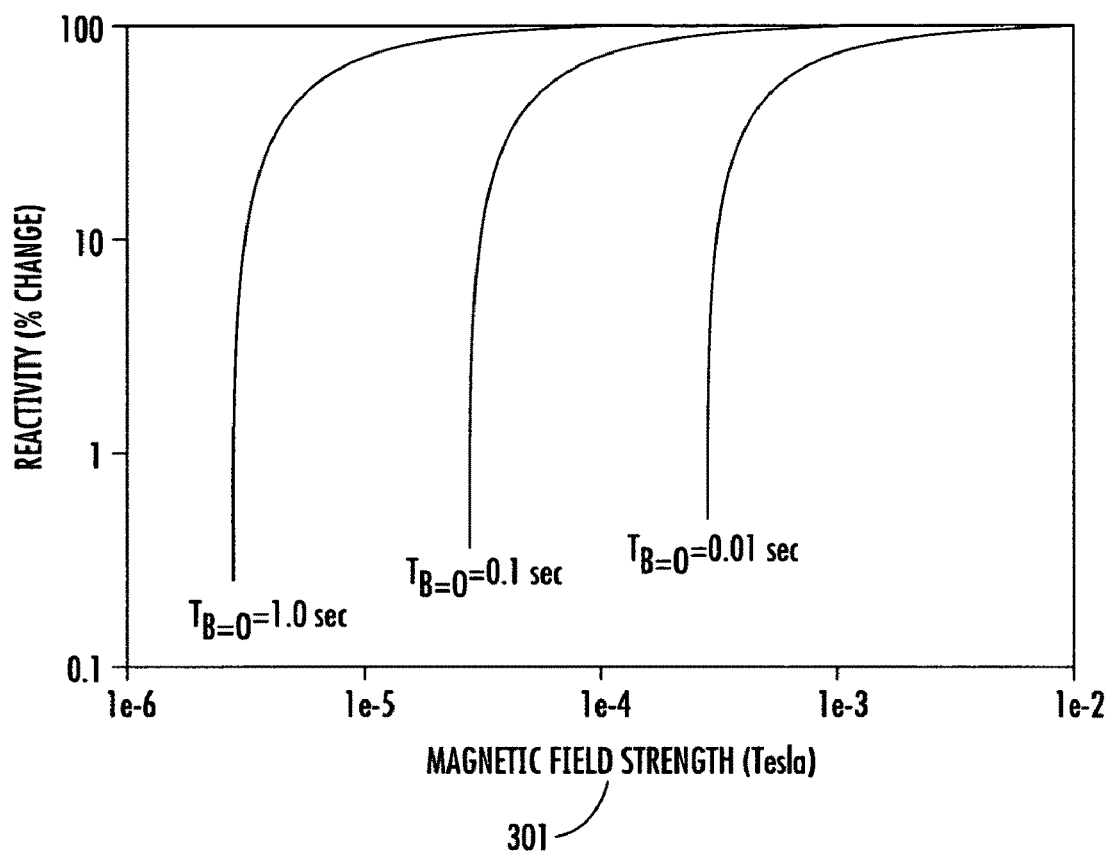
FIG. 3 is a graph depicting a bio-effect of CaCaM binding.

Thus, saturation occurs as field strength grows: further increases in amplitude result in ever smaller relative changes in kinetics. It is important to note that, since the Larmor frequency increases linearly with increasing field strength, for a given target system (i.e., specific binding lifetime), effects will be limited to a narrow range of MFs. Referring to FIG. 3 which depicts a graphical representation of a bio-effect for CaCaM binding with increasing field strength derived from equation (16). For example, for a binding time of 0.1 sec, field strengths 301, below about 10 μT are expected to be ineffective, whilst saturation will occur as the field strength approaches several mT.

LP can affect targets other than bound charged ions. For example, the water molecule carries partial charges, resulting in water's unique chemical characteristics. The resulting strong electric polarization causes water molecules in cells and tissues to form organized, polarized hydration layers, such as the inner and outer Helmholtz layers observed around charge carriers and charged membranes. These bound waters themselves are likely to be subject to LP as applied magnetic fields introduce coherence into the thermal fluctuations of hydration layers via LP. The resultant change in hydration orientation angles alters the potential energy of hydration and thus local dielectric constant $\in(t)$ at the binding site kinetics of binding processes moving through the Helmholtz planes thus depend on LP.

Figure 4:
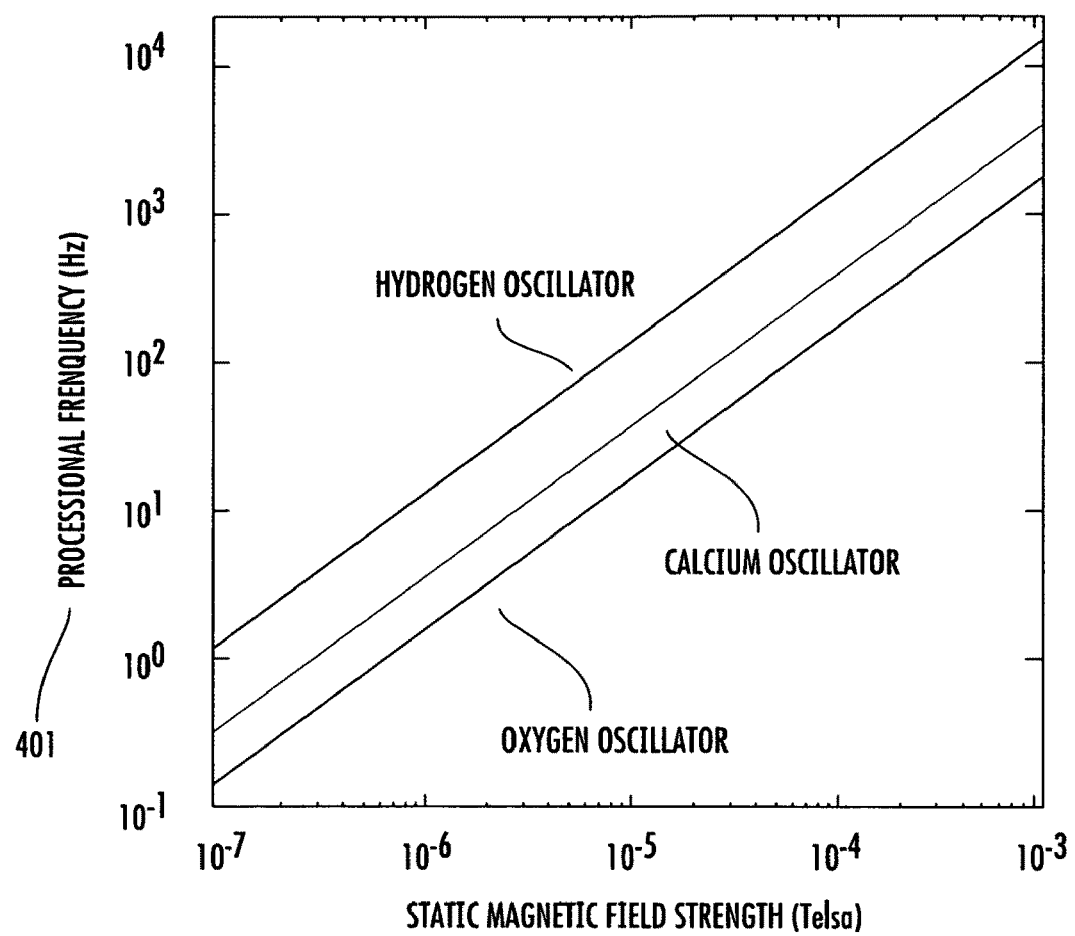
FIG. 4 depicts precessional frequencies of Ca, and oxygen and hydrogen arms of a water molecule.

Since Larmor frequencies for oxygen and hydrogen arms of water also lie near Ca2+ frequency, observations of bio-effects near the Larmor frequency may also be attributable to precession of the water molecules themselves or complexes of hydrated ions, for which the gyromagnetic ratio must be estimated before an accurate determination of the Larmor frequency can be made. FIG. 4 illustrates precessional frequencies 401 for Ca and the arms of water molecules, from equation (1).

AC and AC DC combined resonance are described below according to an embodiment of the present invention.

The current invention aims to take advantage of the conditions such as resonance and particular changes with field strengths and frequency that are intrinsic to LP. The relative parallel or perpendicular orientation of the AC and DC fields is shown to be a critical determinant of the strength and direction of bio-effects. Bio-effects due to LP are dependent upon the amplitudes, frequencies, and spatial directions of all spatiotemporal components of the MF. The precise reactivity of the biological target can be computed, as a function of target physicochemical characteristics and magnetic field characteristics in order to take advantage of specific dose-responses, resonance phenomena such as maxima and minima of reactivity, and treatment regimes that are programmed to take advantage of the specifics of LP.

Resonance conditions are described below according to an embodiment of the present invention.

The LP mechanism yields resonance behavior for a wide variety of combinations of AC and DC MFs, including the geomagnetic field. These resonances are conditions for which maxima, minima or other bio-responses, specifically characteristic of LP, are expected for specific spatiotemporal MF conditions. These specialized conditions can be employed to develop innovative means of maximizing, minimizing, enhancing, inhibiting, or otherwise modulating the bio-responses to applied and ambient MFs. Although the specific examples shown below employ sinusoidally varying AC MFs, LP conditions may be computed to determine specific resonance conditions for any arbitrary combination of DC and non-sinusoidally varying MF waveforms.

LP resonances will be considered to be the computation of resonance conditions through any means that employs the dynamics of LP in order to compute resonance conditions. For illustrative purposes, several methods of computing resonance conditions are illustrated below. However, due to the complexity of the possible orbits of the precessing oscillator and the complexity of bio-molecules generally, it is not possible to treat in detail all possible methods of computing resonances.

AC magnetic field bio-effects are described below according to an embodiment of the present invention.

When an AC magnetic field is added to a DC field a break in the spatiotemporal symmetry of Larmor precession results due to periodic reversals in precession direction with changing AC phase and amplitude, and the interaction with DC magnetic fields in perpendicular or parallel orientations. This symmetry breaking results in modulation, via the applied field geometry, of the oscillator orientation within the binding site and, thus, the probability of contact with a preferred orientation. For example, when the AC phase causes the field strength to be near zero, or causes a destructive interference with DC fields, the oscillator will 'dwell' at a specific region of the binding site, covering very little angular distance until the field rises significantly. Resonance conditions are thus expected for the case of a single AC sinusoidal field alone.

For example, resonance conditions may be assessed through the computation of the mean distance the oscillator spends from a preferred orientation, taken over a time period less than or equal to the binding lifetime:

$$R(x,y,x,t) = c_o \text{mean}((x(t)-o_x)^2 + (y(t)-o_y)^2(z(t)-o_z)^2)^{1/2}) \tag{17}$$

where $c_o$ is a constant, $x(t)$, $y(t)$ and $z(t)$ are the spatial components of the precessing oscillator, the $o_i$ are the spatial components of a preferred orientation. Clearly, the actual preferred orientation(s) determines the specific reactivity. However, as mentioned above, given a specific biomolecular environment, $R(t)$ will take a specific form.

Figure 6:
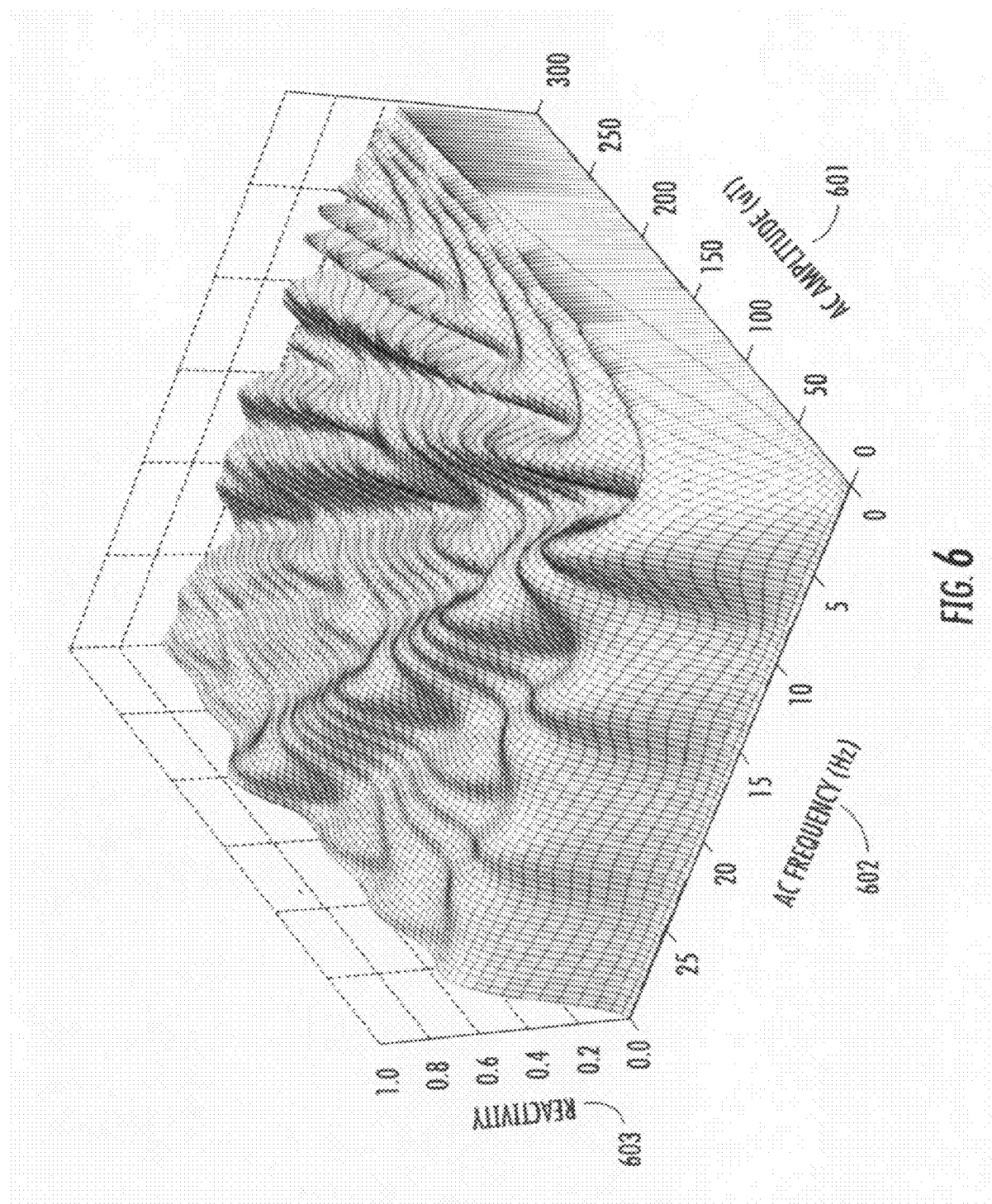
FIG. 6 illustrates reactivity for AC magnetic field bioeffects.

To illustrate the basic characteristics of LPM, examples provided here employ an arbitrary location for the preferred orientation. $R(t)$ can be computed via the parametric equations for an oscillator precessing at Larmor angular frequency $\omega_L$ in the plane perpendicular to the resultant magnetic field:

$$\omega_L = \Gamma B_r = \Gamma (B_{perp}^2 + (B_{para} + B_{ac} \cos(\omega_{ac} t))^2)^{1/2} \tag{18}$$

where Br is the resultant field from the perpendicular, Bperp, and parallel, Bpara, components of the DC field, and the AC field component, Bac, having frequency ωac. As shown in FIG. 6 having AC Amplitude plotted an the x-axis 601, AC frequency plotted on the y-axis 602 and reactivity plotted on the z-axis 603, due to the specific dynamics of LP, the Larmor frequency due to the AC field is time-varying, resulting in a complex modulation of the mean distance from a specific preferred orientation.

AC DC parallel field combination is described below according to an embodiment of the present invention.

Figure 5:
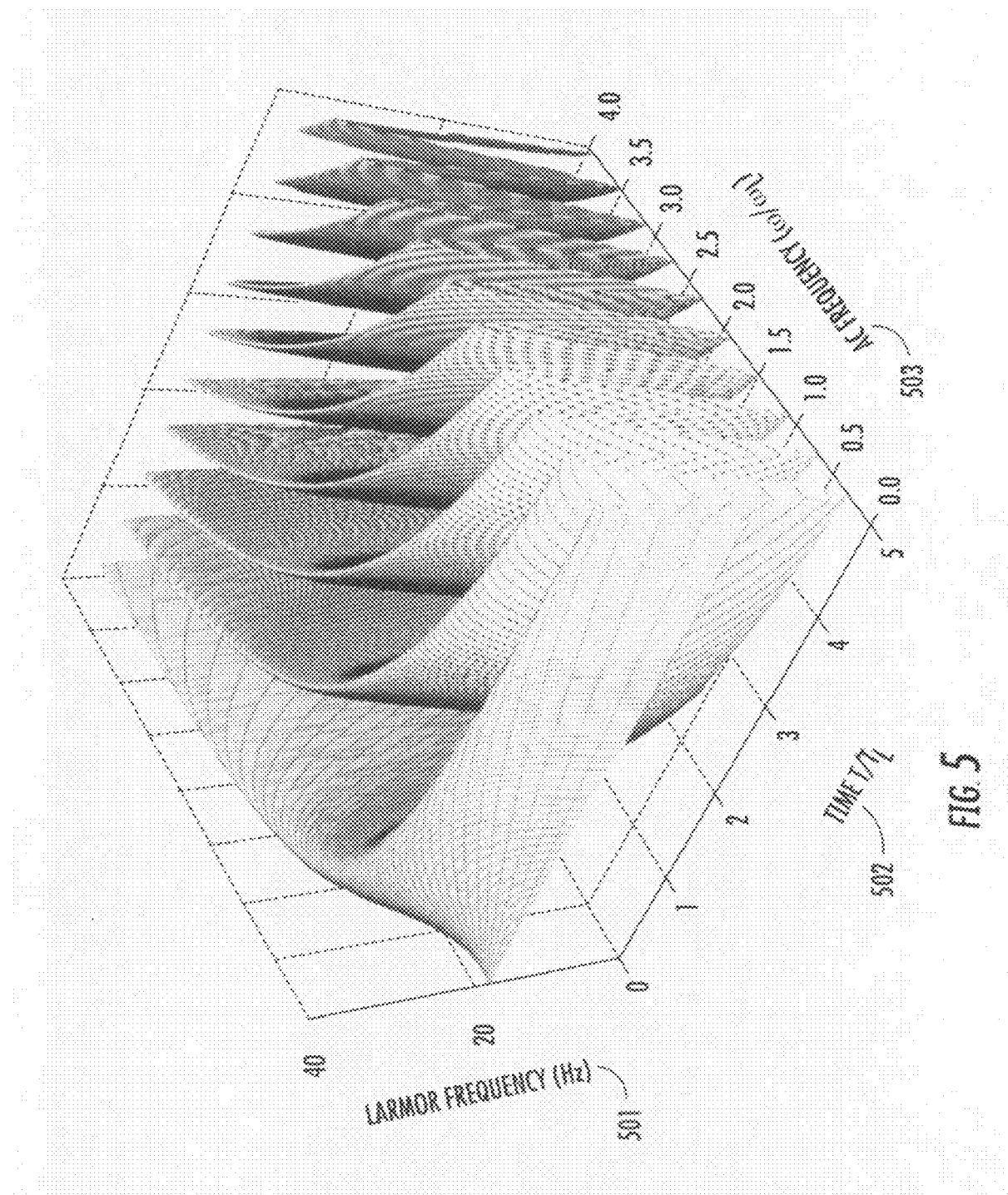
FIG. 5 depicts Larmor Precession frequency of Ca for parallel superposition of 50 µT AC and DC magnetic fields.

For the case of an alternating MF aligned parallel to a static (DC) field, the angular area swept out per unit time, A(t), increases linearly with time bound. For AC/DC parallel combination, $B_r = B_o + B_1 \cos(\omega t)$, so that in general, the Larmor frequency, $\omega_L = \Gamma B_r$ will be a time-varying function of both AC and DC amplitudes. FIG. 5 shows the Larmor frequency 501 for Ca from equation (1). FIG. 5 depicts Larmor Precession frequency of Ca for parallel superposition of 50 μT AC and DC magnetic fields. $T/T_L$ is the ratio of time 502 elapsed in units of one period of the DC field Larmor frequency, and $\omega/\omega_L$ is the ratio of AC frequency 503 in units normalized to the ratio of AC frequency to DC Larmor frequency. The total angular distance traversed by the oscillator is given by the integral of the absolute value of the Larmor frequency:

$$A(t) = C_o \int_0^t |\omega_L| dt = \frac{C_o}{2m} \int_0^t |\vec{B_o} + \vec{B_1}\cos(\omega_{AC} t)| dt \quad (19)$$

where $\omega_L$ is the Larmor frequency; $\vec{B_o}$ is the DC MF vector; $\vec{B_1} \cos(\omega_{AC} t)$ is the AC MF, with frequency $\omega_{AC}$; m is the mass of the bound oscillator; and $C_o$ is a proportionality constant. A(t) may be evaluated for any ion or ligand, any combination of AC and DC MFs with any relative orientation, and is in general a function of target gyromagnetic ratio and DC/AC MF geometry.

The total angular area A(t) swept by the oscillator over time is determined by the Larmor frequency:

$$A(t) = C_o \int_{t_0}^{t_1} \omega_L dt \quad (20)$$
$$= \frac{C_o}{2m} \int_{t_0}^{t_1} [B_o + B_1 \cos(\omega_{AC} t)] dt$$
$$= \frac{C_o}{2m} \left[ B_o(t_1 - t_o) + \frac{B_1}{\omega_{AC}} [\sin(\omega_{AC} t_1) - \sin(\omega_{AC} t_0)] \right].$$

Figure 7C:
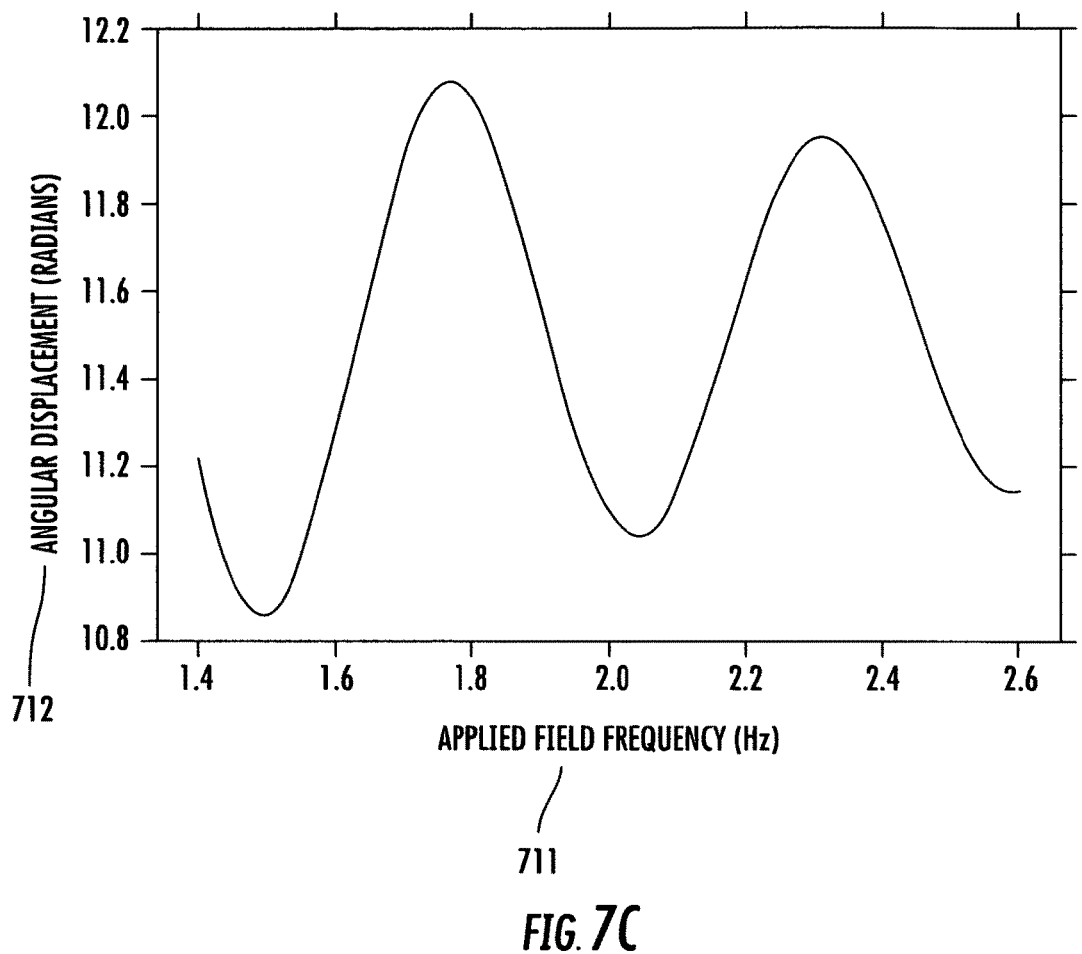
FIG. 7C is a graph that illustrates reactivity for an AC/DC parallel magnetic field combination.

Thus, reactivity is a function of the bounds of integration in equations (19) and (20) and the time-varying Larmor frequency. Because the bounds of integration represent the binding lifetime, the position of resonances will in general be dependent upon the kinetics of the target system, and thus, not be dependent solely upon the Larmor frequency of the binding species. FIGS. 7A and 7B show the dependence of total angular displacement upon kinetics for Ca in AC=DC=50 μT parallel field combination. FIG. 7B, right hand plot 701, for systems with relatively short binding lifetimes, for example, up to 3 times the DC Larmor period, broad resonance peaks occur. and may be predicted via equation (20). FIG. 7A, left hand plot 702, shows the dependence of total angular displacement upon kinetics as the binding lifetime approaches 1 second or more (18 times the Larmor period), whereby resonances disappear substantially.

The relative amplitudes of the AC and DC fields are also critical in determining the height and position of resonance conditions. Because the Larmor frequency is dependent on the resultant AC+DC amplitude, for AC>DC the oscillator will undergo periodic changes in precessional direction. The result shows addition of an AC MF to the precessing oscillator can either accelerate or inhibit its time to reach a reactive orientation. For parallel AC/DC field combinations, the results are remarkably similar to reported experimental verifications of IPR, and suggests LP as a viable alternative mechanism for weak DC and AC MF bio-effects. The resulting resonance conditions may be reflected in the conditions employed by Koch. FIG. 5 shows the prediction of the LP model for DC=37 μT, AC=1.7 μT, for applied AC fields ranging from approximately 18 to 35 Hz, or about 1.4-2.6 times the Larmor frequency for Ca in the 37 μT DC field. These calculations were made for a target system with a lifetime of about 4 times the period of the Larmor frequency for Ca in the DC field. The results compare favorably to FIG. 8 of the published Koch experiments.

Figure 8:
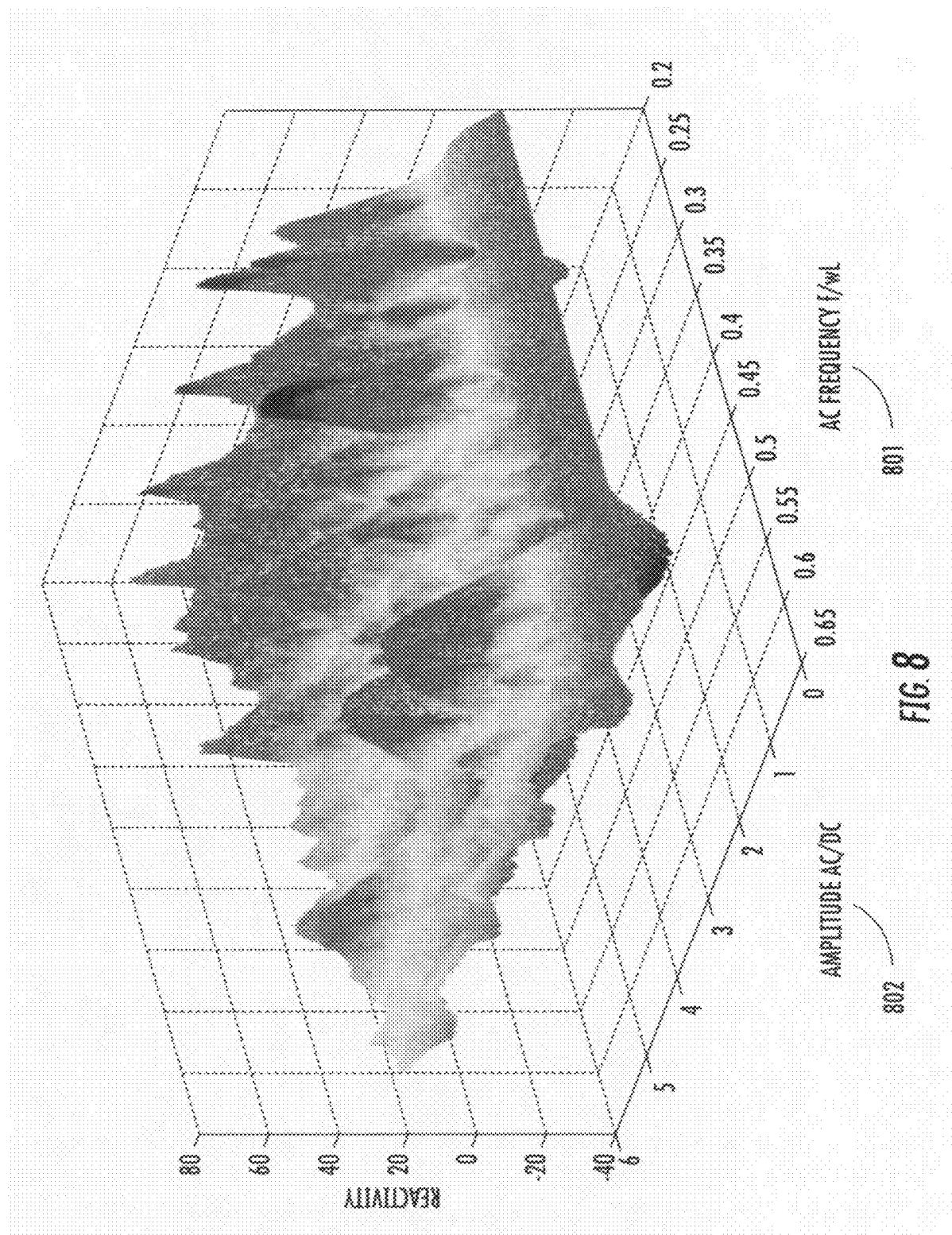
FIG. 8 is a graph of typical reactivity of mean deviation from random oscillator orientation, as a function of AC frequency and amplitude.

Additionally for a parallel AC and DC MF combination, complex resonance conditions are expected for specific AC amplitudes and frequencies, based upon the coherent precessional motion of the oscillator. For example, as shown in FIG. 8 the mean deviation from a random distribution (i.e., mean oscillator position=π) of oscillator positions varies with AC frequency 801 and amplitude 802. Complex deviations in FIG. 8, are produced via equation (20), for mean(A(t))–π. The position of the peaks and troughs in FIG. 8 provides an example of one means of determining the specific AC/DC field combinations that are expected to produce enhanced or diminished bio-effects.

Figure 9B:
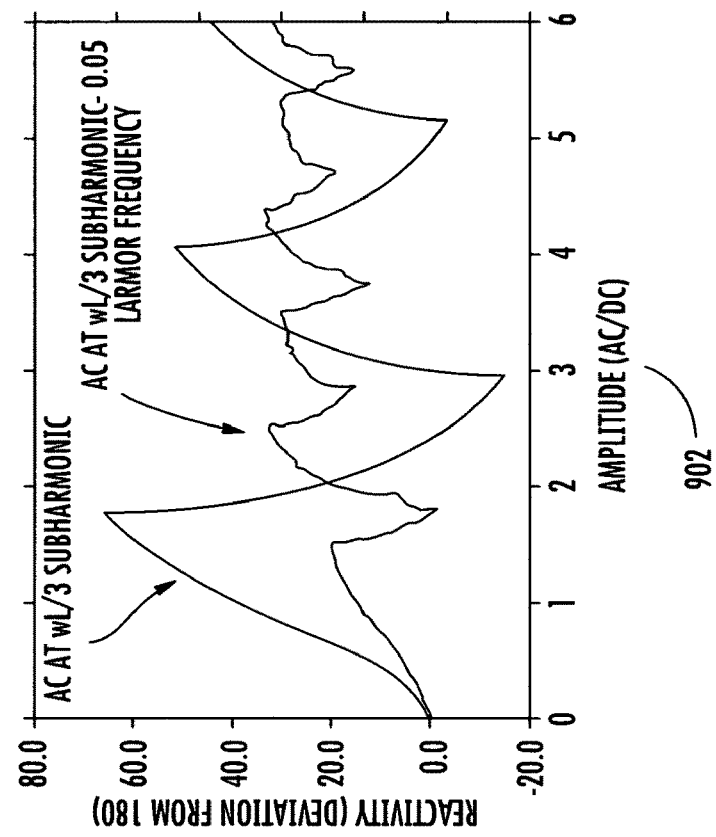
FIG. 9 depicts a comparative example of on-resonance and off-resonance behavior for parallel AC/DC magnetic field combinations.
Figure 9A:
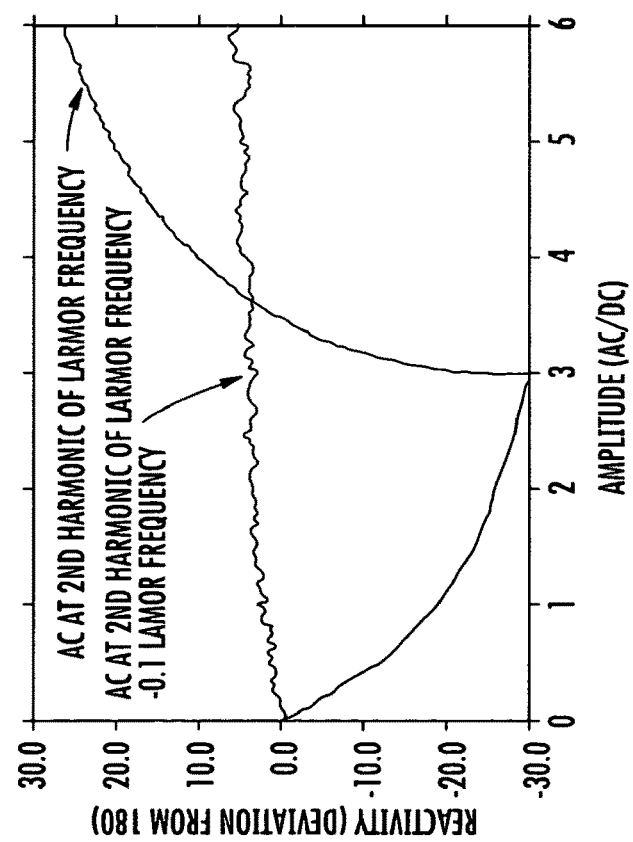

FIG. 9 shows slices of FIG. 8 at specific AC frequencies, to detail the structure of resonances, and the effect of shifting to slightly off-resonance frequencies. For example, FIG. 9, left hand plot 901 shows that reactivity as a function of AC/DC amplitude, at the $2^{nd}$ harmonic of the Larmor frequency (2×ωL) and slightly off-resonance at ωL–0.1 ωL. Note that directly on the Larmor harmonic, a pronounced resonance occurs for AC=3×DC amplitude. Shifting the AC frequency by 10% of ωL (5% of AC at $2^{nd}$ harmonic) effectively destroys this resonance. Thus, precise knowledge of the LP conditions for a system allows for accurate generation of AC/DC combinations that will produce resonances, and clinically significant bio-effects.

More complex resonance behaviors occur at other AC frequencies, including sub-harmonic frequencies of the Larmor frequency. For example, FIG. 9, right hand plot 902 shows resonance conditions for AC frequency=ωL/3 and ωL/3–0.05 ωL. For these conditions, a slight shift in AC frequency (0.05 ωL) results in an increase in the number of resonance peaks, and a concomitant decrease in the resonance strength.

AC DC perpendicular field combination is described below according to an embodiment of the present invention.

For the case of an AC MF in perpendicular orientation with a DC field, the spatial direction of the resultant MF varies in time, breaking the cylindrical symmetry of the previous example. It has been suggested previously that the resultant excursion of the oscillator out of the cylindrical geometry will result in changes in bio-effects, due to changes in the angular area A(t) swept per unit time. Thus, both the Larmor frequency and axis of precession are time-varying, and the accumulation of angular area given by equation (17) will be modulated by the component of the precession in the z-direction. By geometry, the results are:

$$Z(t) = C_z \frac{B_o \cos(\omega_{Lresultant} t))}{\sqrt{B_o^2 + (B_1 \cos(\omega_{AC} t))^2}}; \quad (21)$$

$$A(t) = C_o \int_{t_0}^{t_1} \omega_{Lresultant} dt.$$

where $$\omega_{Lresultant} = \Gamma B_r = \Gamma (B_o^2 + (B_1 \cos(\omega_{AC} t))^2)^{1/2}. \quad (22)$$

Due to the excursions of the axis of precession away from the z-axis, the Larmor frequency for perpendicular fields varies with time in a manner somewhat more complicated than that for the case of parallel AC/DC combination. The complicated dynamics that arise imply that changes in reactivity are caused by both the AC-modulated Larmor frequency as well as the time-varying changes in precession axis.

It has been established that resonances will occur when excursions of the oscillator attain their maxima, i.e., the AC frequency is an integer multiple of the Larmor frequency. This means that resonances may be observed for perpendicular field configuration by scanning along increasing AC field strength, holding DC constant. For example, FIG. 10, left hand plot 1001 shows the excursion of the oscillator axis from the z-axis from equation (21), as a function of the ratio $B_1/B_o$, shown here for AC frequency=Larmor frequency of DC field strength. Note the appearance of regions of constant oscillator excursion, equally spaced at $B_1=2nB_o$. A(t) achieves maxima and minima for these conditions, computed as the time average of the z-declination from equation (21), taken over the binding lifetime=7 Larmor periods of the DC field shown in FIG. 10, left hand plot. The shape of the landscape in FIG. 10, left hand plot 1001, and appearance of larger numbers of minor resonances with increasing AC strength, reflects the increasingly complicated dynamics of the oscillator with increasing AC amplitude. FIG. 10, right hand plot 1002, shows the reactivity A(t) for these conditions. Note that both inhibitory and excitatory responses occur, corresponding to the extrema shown in the left hand plot 1001. This therapeutically relevant example indicates that for systems governed by the ion binding process considered, a magnetic field can be configured such that inhibition of the process may be obtained at AC amplitude≈twice DC amplitude, and excitation, or enhancement of the process may be obtained at AC amplitude ≈4 times DC amplitude.

Arbitrary combinations of AC and DC magnetic fields are described below according to an embodiment of the present invention.

Larmor precession conditions may also be predicted based upon the mean distance of the oscillator from a preferred orientation favoring or impeding the molecular binding process. Resonance conditions may be computed for AC alone, AC parallel to DC, AC perpendicular to DC, and combined parallel and perpendicular magnetic fields. For example, LP conditions allow for the precise calculation of the trajectory of the precessing oscillator:

$$\vec{r}(x,y,x,t) = x(t)\hat{i} + y(t)\hat{j} + z(t)\hat{k} \quad (23)$$

Where x(t), y(t) and z(t) are found through solution of the equation of motion of the oscillator, generalized from equation (2) to the 3-dimensional case:

$$\frac{d^2\vec{r}}{dt^2} = -\beta \frac{d\vec{r}}{dt} + \gamma \frac{d\vec{r}}{dt} x B_o k - \omega^2 \vec{r} + \vec{n}, \quad (24)$$

and $\hat{i}, \hat{j}, \hat{k}$ are the unit vectors in the three spatial directions, x, y and z.

Figure 11:
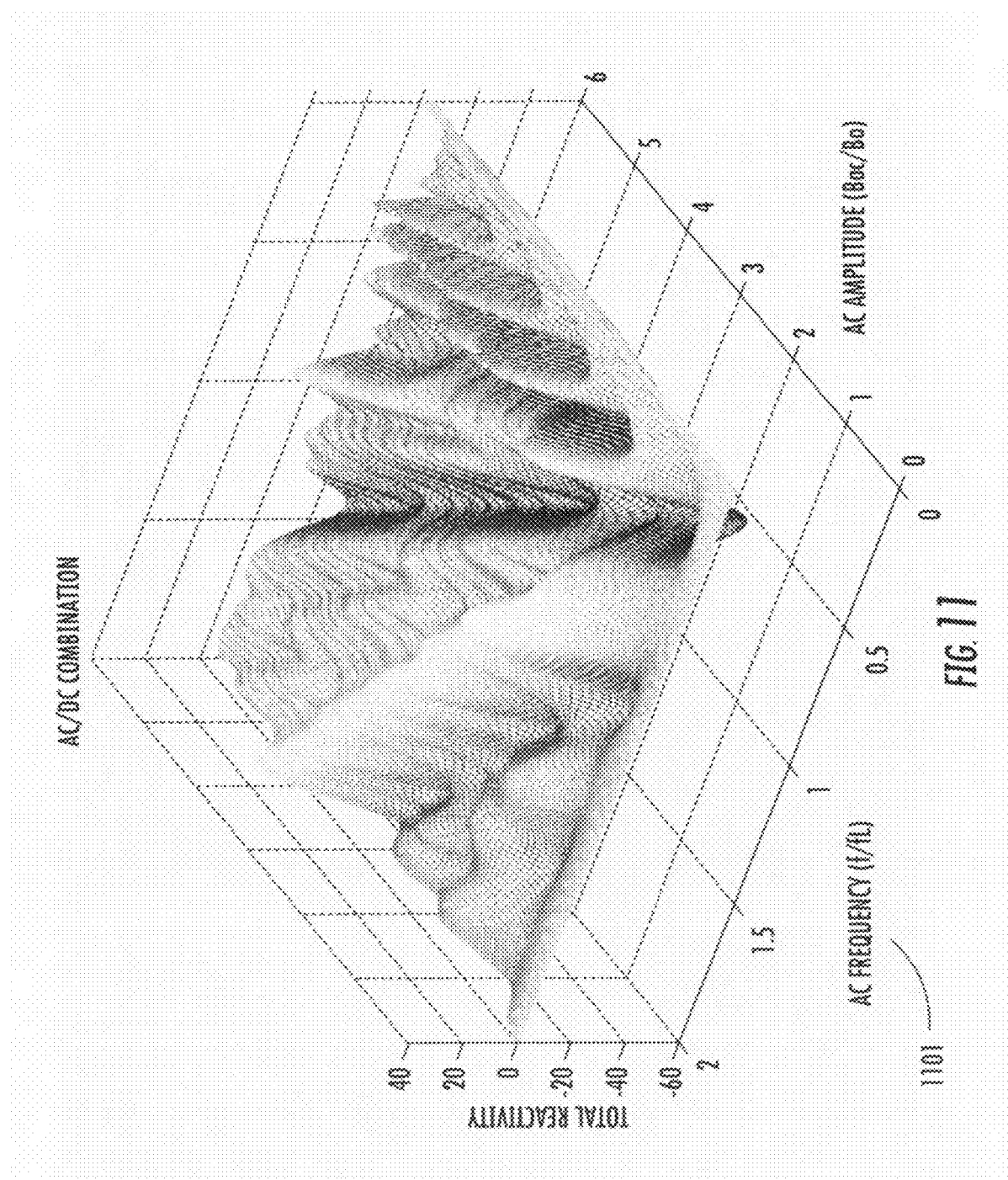
FIG. 11 is an example of LP conditions for combined AC/DC field combinations.

FIG. 11 shows the reactivity, from equations (17), (18) and (23), via mean distance to a preferred orientation for an arbitrary AC/DC field combination, as a function of AC field frequency 1101 and the ratio of AC to DC field strengths. It can be seen that specific resonance conditions exist, yielding both excitatory and inhibitory responses. By choosing specific combinations of AC and DC parallel and perpendicular magnetic fields, specific resonance conditions can be applied to the biological target.

Figure 12A:
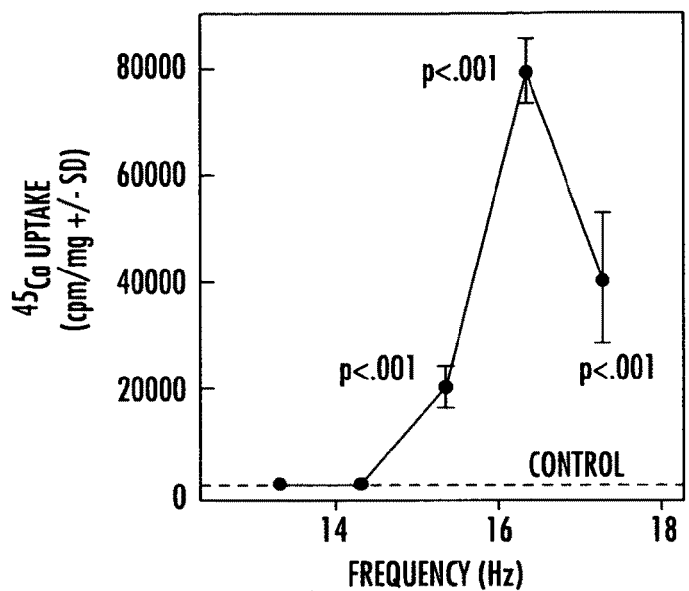
FIG. 12 is a graph of results of an experiment with calcium flux in bone cells, on the top right showing a region of the LP resonance landscape relevant to this experiment and on the bottom a relevant predictive frequency response.
Figure 12B:
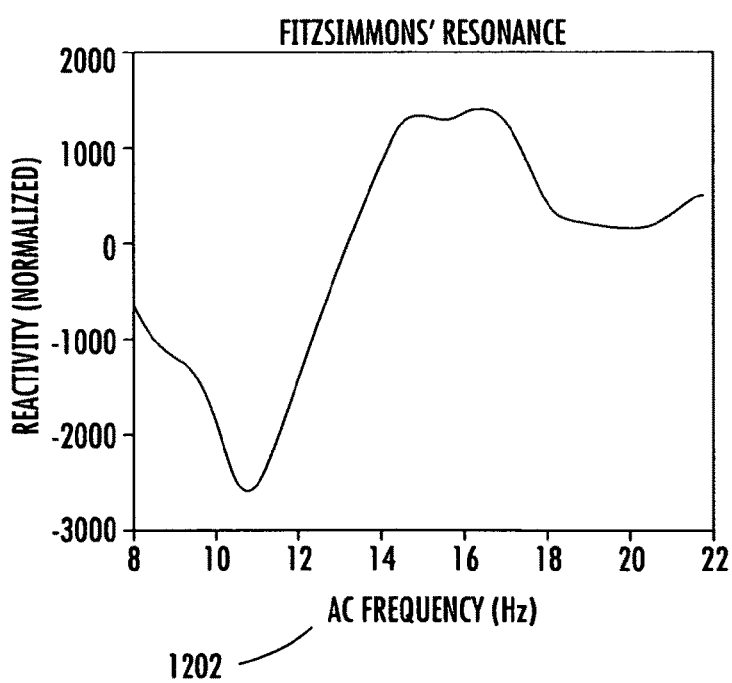
Figure 12C:
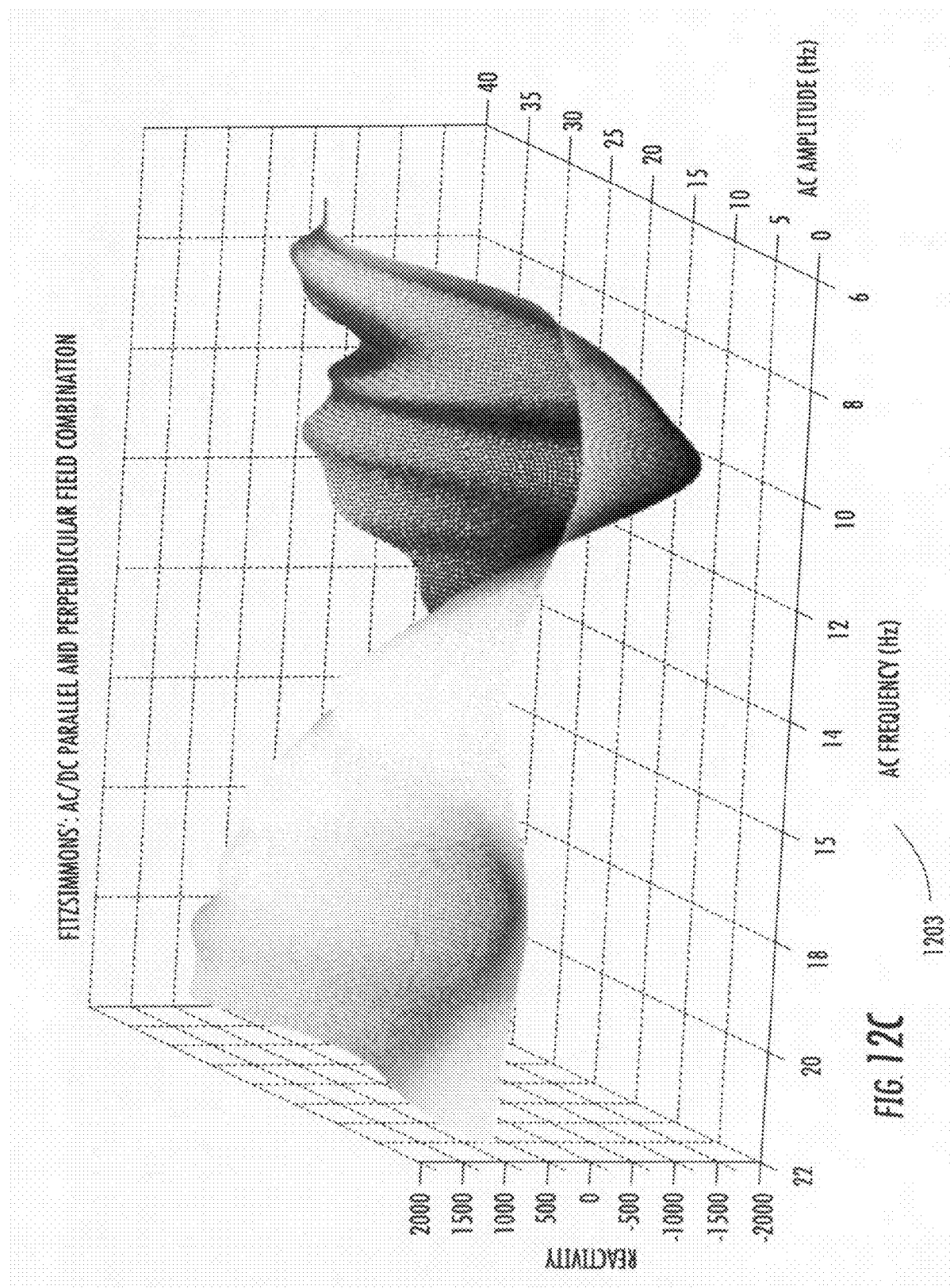
Figure 13A:
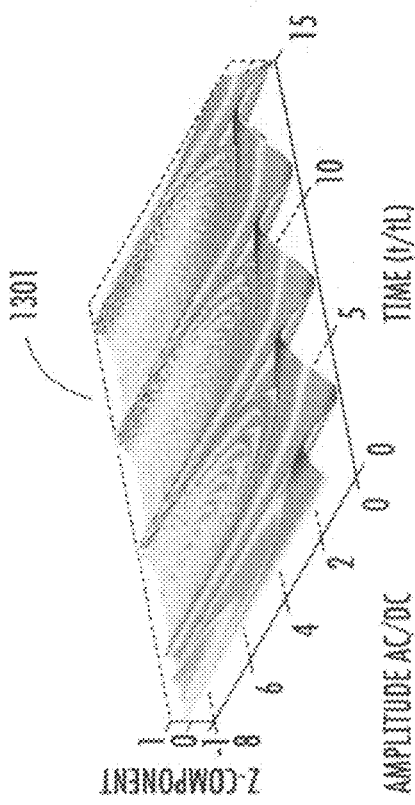
FIG. 13 illustrates on the top left 1301 is a resonance landscape for specific field configuration shows z-component of oscillator trajectory, subject to applied AC/DC parallel and perpendicular field combination with the bottom left showing the reactivity determined by mean z-excursion displacement from zero shows both inhibitory and excitatory responses while the top right shows the resonance landscape for modified field configuration produces predictable change in reactivity as shown on the bottom right graph.
Figure 13B:
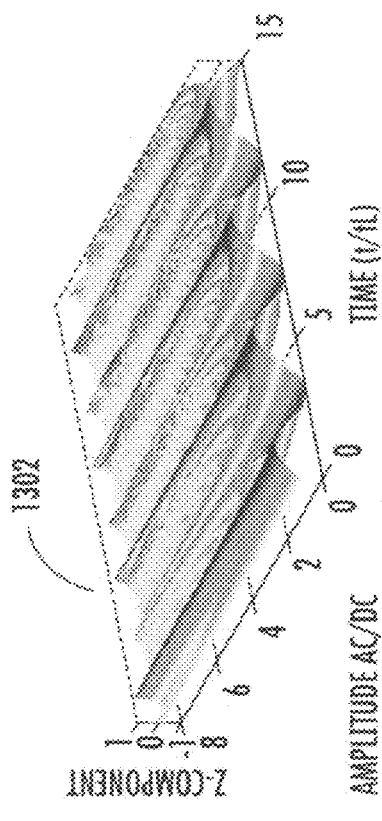
Figure 13C:
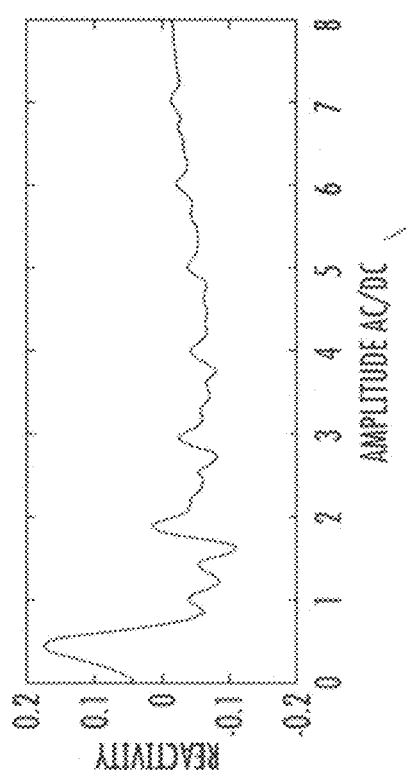
Figure 13D:
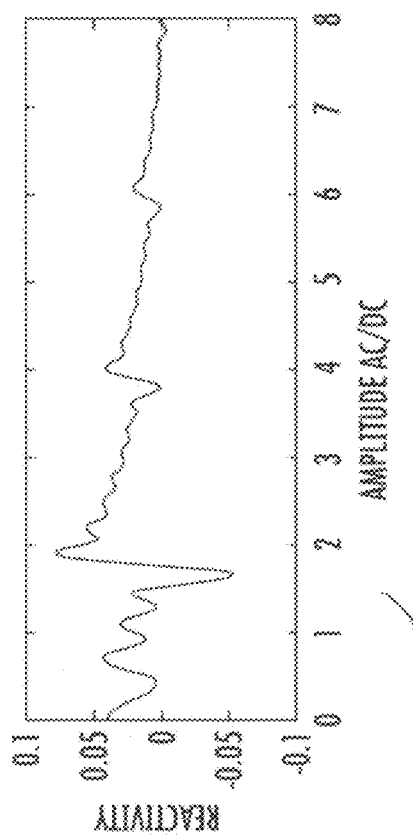

FIG. 12 shows the results of an experiment measuring Ca flux in bone cells. These results have not been adequately explained to date and are clinically relevant for the configuration of bio-effective EMF signals. FIG. 12, top left 1201, shows the resonance observed experimentally, with a prominent peak in Ca flux in the range of 16 Hz for the applied AC field. FIG. 12, top right 1203, shows the region of the LP resonance landscape relevant to this experiment, as computed via equations (17), (18) and (23). The precise location of resonances may be found, given knowledge of the detailed shape of the relevant resonance 'landscape.' FIG. 12, bottom 1202, shows a slice through the region at AC=20 µT providing the relevant frequency response, successfully predicting results of the experiment. Thus, knowledge of LP conditions for a specific target system allows for the prediction of the relevant bio-effective waveform.

Thus, through detailed knowledge of the solution to equation (24), and thus the LP resonance landscape, specific MFs may be configured to yield therapeutically relevant excitation and inhibition. For example, FIG. 13, left top 1301, shows reactivity for AC DC combined parallel/perpendicular configuration determined by mean z-excursion displacement from zero shows both inhibitory and excitatory responses. For this case, the AC frequency is equal to 0.5 times the Larmor frequency of the DC parallel MF. Note that a specific pattern of responses is obtained for the field configuration, as shown in the plot on the lower left 1304. In comparison, FIG. 13, top right 1302, shows the z-excursion of the oscillator for the same conditions, except with the frequency of the AC MF now equal to 1.0 times the Larmor frequency of the DC parallel MF. This change in AC frequency results in a predictable change in reactivity, as shown in FIG. 13, lower right plot 1303.

Larmor Precession—bio-effective fields generated coupling with ambient fields is described below according to an embodiment of the present invention.

The present invention comprises a method of precisely controlling the magnetic field environment at the biological target in order to produce a magnetic field configuration designed to produce specific bio-effects, according to empirical data or a mathematical model.

The present invention comprises a configuration of coils and/or permanent magnets, in any geometric arrangement, including triaxial, biaxial or uniplanar, that delivers a magnetic field to a target. All spatiotemporal components of the magnetic field are controlled in order to deliver a specific magnetic field configuration to the biological target. The ambient geomagnetic and environmental magnetic field is monitored in order to use these components for the purpose of configuring the applied bio-effective field.

In general, the magnetic field applied to a biological target by a system of coils is the superposition of: 1) the field $B_{device}$ due directly to the currents applied to the coils; 2) the field $B_{ambient}$ due to ambient sources such as the local geomagnetic field (on the order of 0.5 Gauss and varying geographically in magnitude and direction) and all other sources such as medical equipment, power lines, etc. The total resultant magnetic field is:

$$\vec{B}(x,y,x,t)_{total} = \vec{B}(x,\vec{y},x,t)_{device} + \vec{B}(x,y,x,t)_{ambient}. \quad (24)$$

Thus, total magnetic field may be completely controlled by selecting the device magnetic field to superpose in a meaningful fashion with the ambient field. For therapeutic purposes, a mathematical or empirical model detailing the interactions of applied magnetic fields with the biological target may be employed to develop a bio-effective therapeutic field configuration. Rather than shielding the target from ambient magnetic fields, the present invention of these fields to form the final bio-effective field $$\vec{B}(x,y,x,t)_{bioeffective} = \vec{B}(x,\vec{y},x,t)_{device} + \vec{B}(x,y,x,t)_{ambient}, \quad (25)$$

so that the magnetic field required by the device is:

$$\vec{B}(x,y,x,t)_{device} = \vec{B}(x,y,x,t)_{bioeffective} - \vec{B}(x,y,x,t)_{ambient}. \quad (26)$$

The present invention employs this fact, thus utilizing the ambient magnetic field as an integral component of the total specifically configured magnetic field.

The present invention makes a precise measurement of the spatiotemporal components of the ambient magnetic field via a triaxial magnetometer probe. This measurement is then compared to the desired bio-effective magnetic field configuration to produce a magnetic field to be generated by the device via equation (26).

A combined AC/DC magnetic field configuration may be produced by several different methods: triaxial, biaxial, Helmholtz, uniplanar, or arbitrary coil combinations, both with and without the addition of permanent magnets. For example, a given magnetic field may be obtained simply by canceling the ambient field, then adding, through superposition, the desired field components:

$$\vec{B}(x,y,x,t)_{device} = -\vec{B}(x,y,x,t)_{ambient} + \vec{B}(x,y,x,t)_{bioeffective} \quad (27)$$

This approach generally requires the use of triaxial or biaxial coils in Helmholtz configuration.

Thus, for the general case, given an empirical or mathematical model used to determine the bio-effective magnetic field configuration, the following method may be employed:
1) Measurement and cancellation/modulation of undesired components of the ambient magnetic field using appropriate coils and/or permanent magnets.
2) The use of the remaining components of the ambient magnetic field to calculate components of bio-effective field dependent upon ambient values (see Larmor precession example below).
3) The use of the remaining components of the ambient magnetic field to generate components of bio-effective field.
4) The application of additional spatiotemporal field components using appropriate coils and/or permanent magnets, in order to complete the bio-effective field configuration.

Figure 14B:
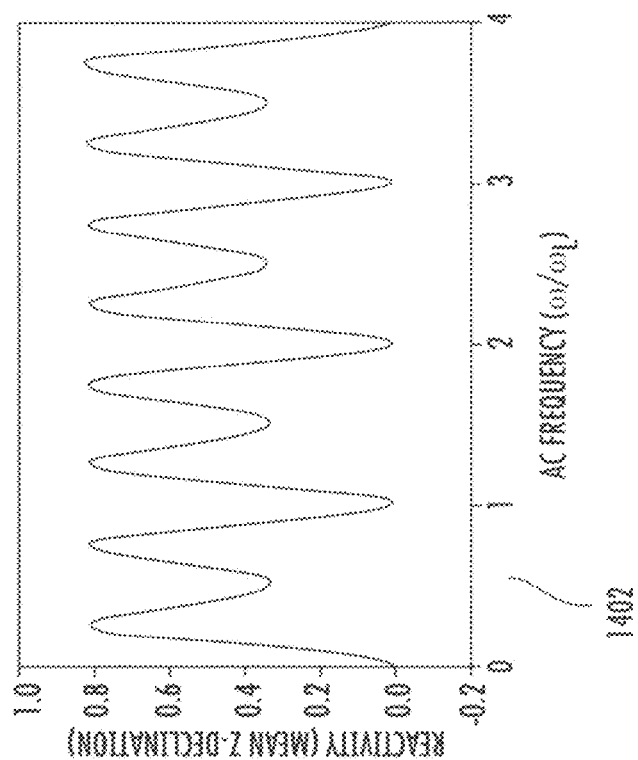
FIG. 14 illustrates LP resonance conditions, on the left 1401 resonance conditions predicted by Larmor precession for AC/DC perpendicular field combination meaning extrema of reactivity, measured via z-declination of the precessing oscillator, occur at ½-integer multiples of the Larmor frequency of the oscillator in the DC field, noting that resonance conditions are dependent upon AC frequency and ratio of AC/DC amplitudes thus location of resonances will depend upon contribution due to ambient fields, and on the right, location of resonances for AC amplitude=0.5 DC amplitude meaning regions of inhibited reactivity occur at integer multiples of the Larmor frequency of the DC field.
Figure 14A:
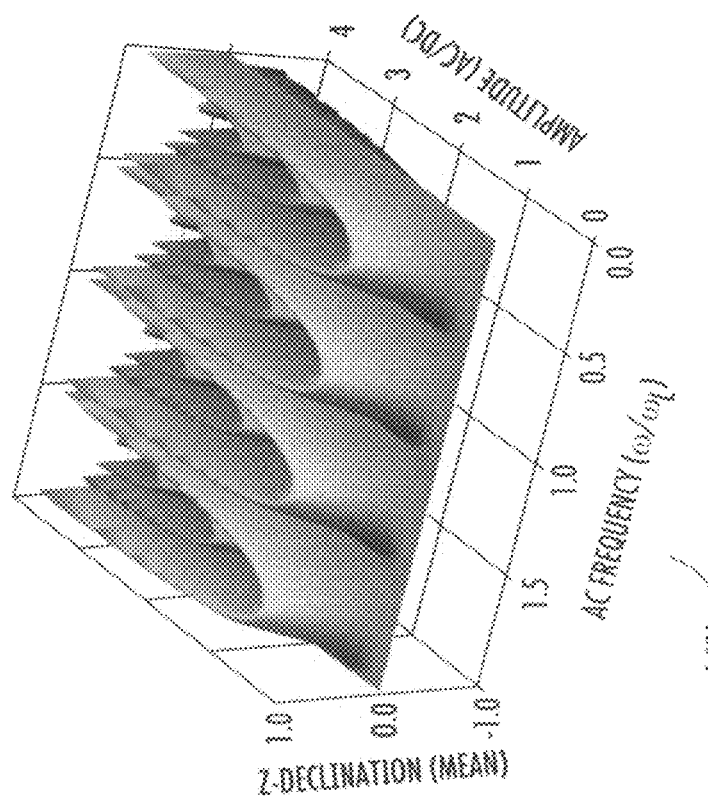

A specific example employing LPM predicts that one bio-effective configuration comprises the combination of a constant (DC) and sinusoidal alternating (AC) magnetic fields, oriented perpendicular to each other. For this configuration, extrema of bio-effects are expected at the Larmor frequency of the target in the DC field, and its' half-integer multiples, as shown in FIG. 1. Such extrema have biological implications of enhancing or reducing the reactivity of the target ion/ligand binding pathway. FIG. 14, left hand plot 1401 shows the structure of these resonances, proportional to z-declination of the precessing oscillator, as a function of AC frequency and the ratio of AC to DC amplitude. Note that the AC frequency is a function of the Larmor frequency of the DC field, so that resonance conditions varying with frequency and AC amplitude are also a direct function of the perpendicular DC field strength. FIG. 14, right hand plot 1402 shows the reactivity as mean z-declination as a function of AC frequency from equation (21), for AC amplitude=0.5 DC amplitude. Note that regions of inhibited reactivity occur at integer multiples of the Larmor frequency. In general, mathematical and empirical models make it possible to configure combined AC/DC magnetic fields targeted towards specific processes with specific bio-responses.

Figure 15B:
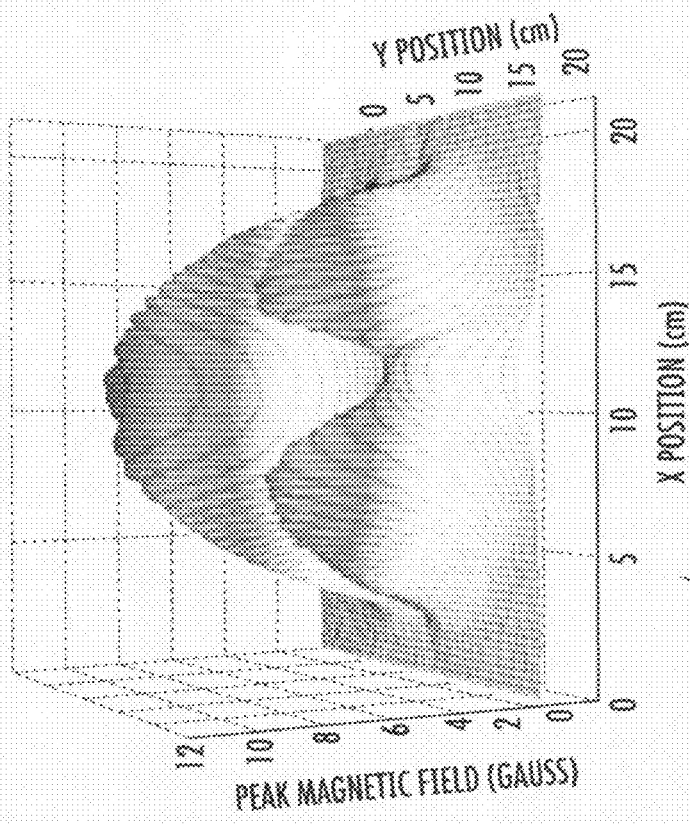
FIG. 15 illustrates spatial components of the magnetic field due to a 6 inch diameter single-turn coil whereby precise knowledge of spatiotemporal components of the field due to the device allow this field to be employed in superposition with the ambient magnetic field to produce a resultant bioeffective field.
Figure 15A:
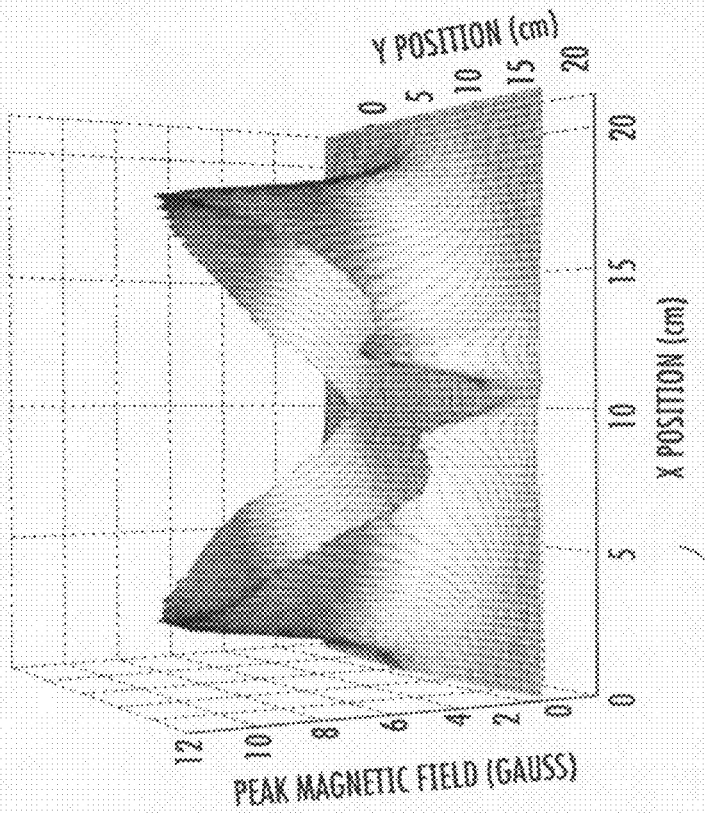
Figure 15C:
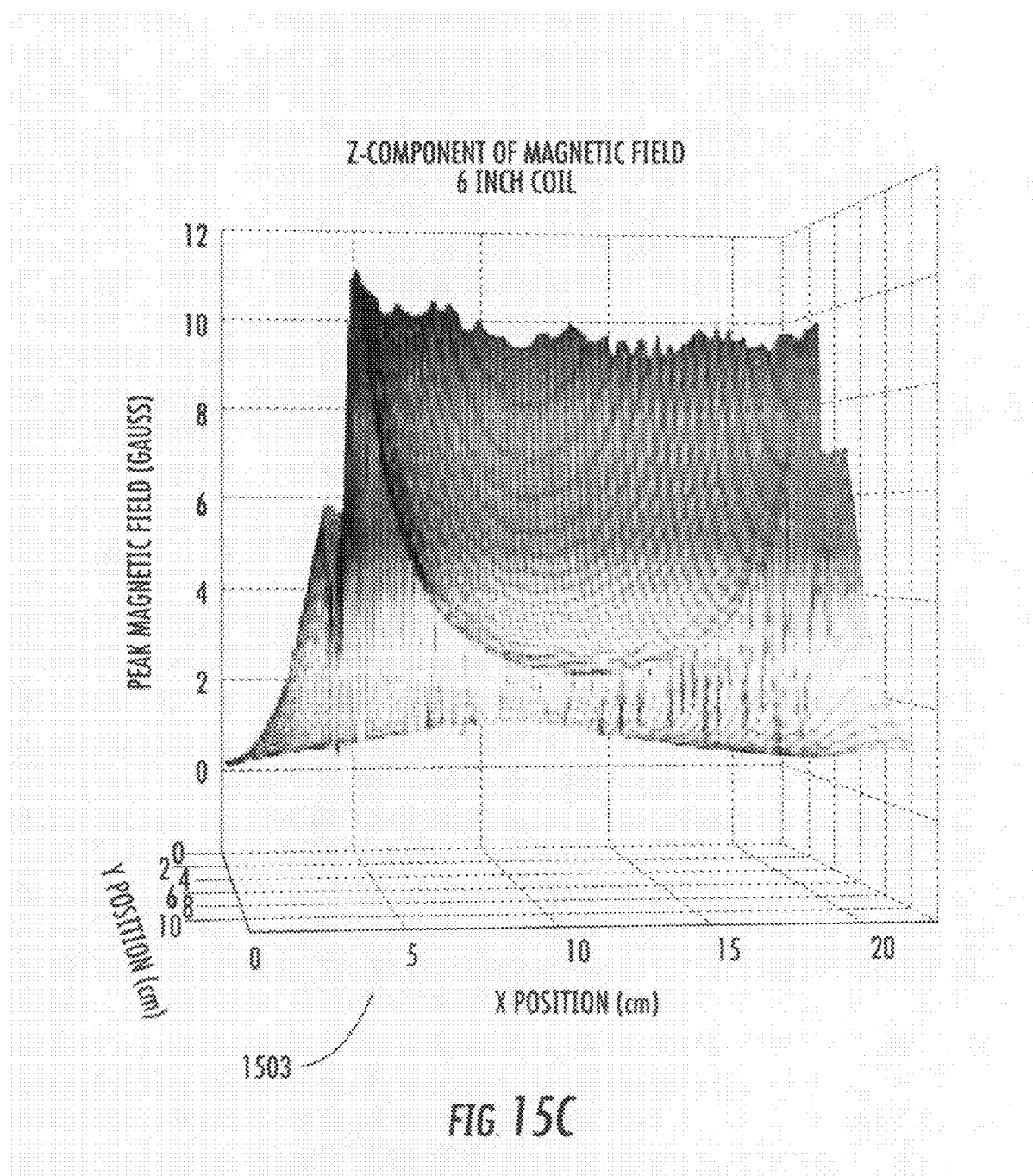

An embodiment according to the present invention makes use of the ambient magnetic field to produce the bio-effective field configuration. For this case, a single planar coil may be employed and measurements of the ambient field components used to generate the bio-effective field via equation (26). A single planar coil may be employed, rather than coils in Helmholtz configuration, because the magnitude and geometry of the field delivered by such a coil is precisely determined by the input current into the coil and may be calibrated though spatial measurements. For example, a 6-inch diameter applicator coil delivers a resultant magnetic field with x, y, and z components that are primarily in the direction perpendicular to the plane of the coil, as illustrated in FIG. 15. Note that, due to the circular symmetry of the system and field cancellation across the axis of the coil, the perpendicular X-Y components yield values close to ambient level (approximately 2 milliGauss) at the center of the coil (FIG. 15, left hand 1501 and middle plots 1502). As shown in FIG. 15, right hand plot 1503 the dominant component of the magnetic field in the central treatment region is the 2.0 Gauss z-component, perpendicular to the plane of the coil.

Thus, for this case of LPM for perpendicular magnetic fields and a single circular coil, measurement of the ambient magnetic field allows for:
1) The cancellation of the z-component of the ambient magnetic field.
2) The use of the remaining x and y components of the ambient magnetic field in order to calculate:
  a) the required frequency of the applied AC magnetic field.
  b) the required AC amplitude (see FIG. 1).
3) The application of an AC magnetic field in the z-direction via a signal applied through the coil.

The field that must be produced by the coil is thus:

$$\vec{B}(x,y,x,t)_{device} = -\vec{B}(x,y,x,t)_{Zambient} + \vec{B}(x,y,x,t)_{AC} \quad (28)$$

Where $B_{Zambient}$ is the z-component of the ambient field, and $B_{AC}$ is the desired AC field.

The resultant field produced will be composed of an AC component oriented along the z-axis, combined with the ambient (DC geomagnetic) component in the x-y plane, fulfilling Larmor precession conditions for the perpendicular AC/DC resonance described above.

Figure 19:
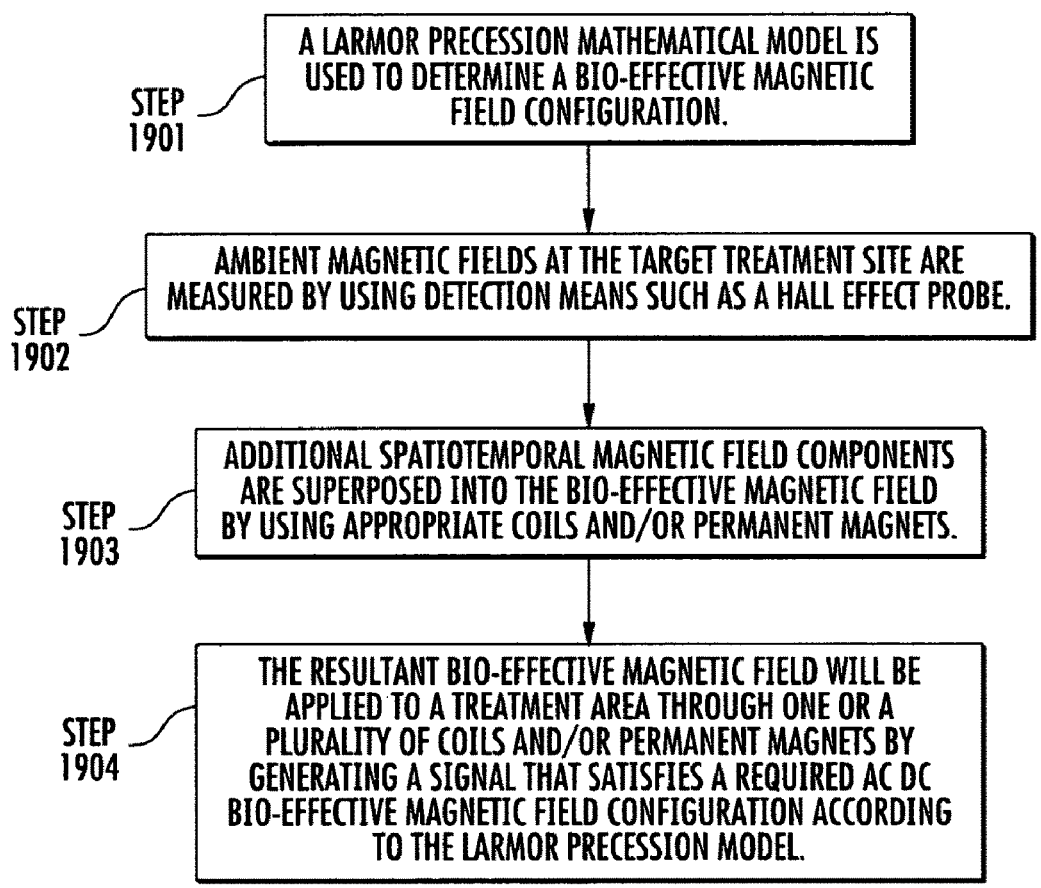
FIG. 19 is a block diagram of a method according to an embodiment of the present invention.

Referring to FIG. 19, wherein FIG. 19 is a flow diagram of a method for configuring a bio-effective magnetic field according to an embodiment of the present invention. A Larmor Precession mathematical model is used to determine a bio-effective magnetic field configuration. (Step 1901) A mathematical model such as that described in equations 17 through 20 can be used for the determination but other mathematical models can be used. Ambient magnetic fields at the target treatment site are measured by using detection means such as a Hall effect probe. (Step 1902) The detected ambient magnetic field can be broken down into components. Some of those components can be partially incorporated into the bio-effective magnetic field by using appropriate coils and/or permanent magnets to cancel and/or modulate any components of the bio-effective magnetic field as described in equations 24 through 27. Additional spatiotemporal magnetic field components are superposed into the bio-effective magnetic field by using appropriate coils and/or permanent magnets. (Step 1903) The resultant bio-effective magnetic field will be applied to a treatment area through one or a plurality of coils and/or permanent magnets by generating a signal that satisfies a required AC DC bio-effective magnetic field configuration according to the Larmor Precession model. (Step 1904)

Figure 20:
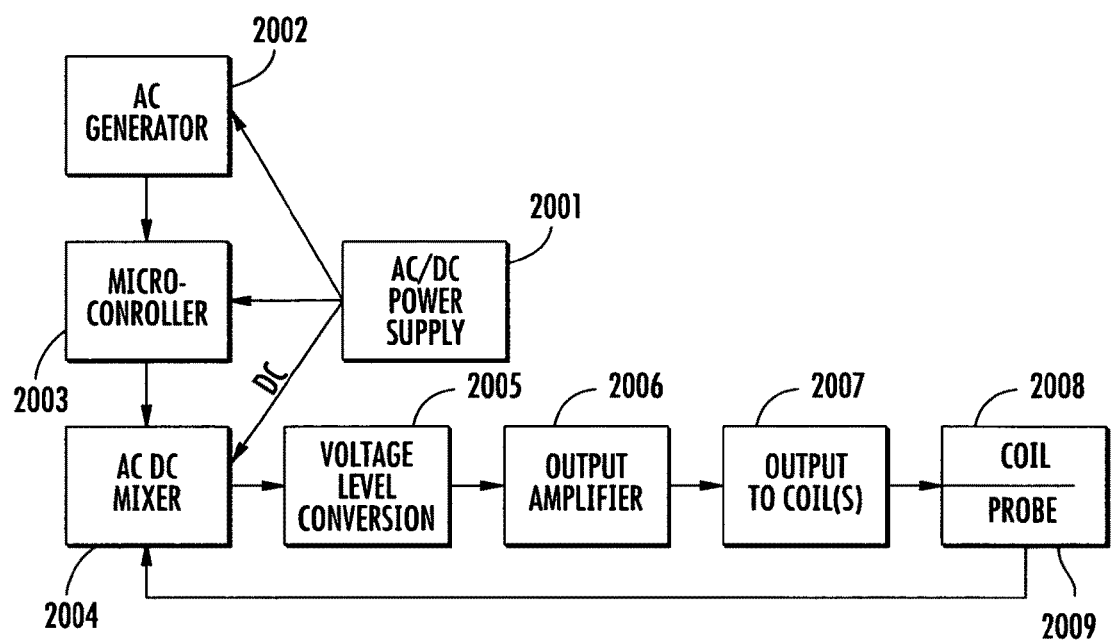
FIG. 20 is a block diagram of an apparatus according to an embodiment of the present invention.

FIG. 20 depicts a block diagram of an apparatus for configuring a bio-effective magnetic field according to an embodiment of the present invention. The bio-effective magnetic field apparatus produces signals that drive a generating device such as one or more coils. The bio-effective magnetic field apparatus can be activated by any activation means such as an on/off switch. The bio-effective magnetic field apparatus has an AC DC power supply 2001. The AC DC power supply 2001 can be an internal power source such as a battery or an external power source such as an AC/DC electric current outlet that is coupled to the present invention for example by a plug and wire. The AC DC power supply 2001 provides power to an AC generator 2002, a micro-controller 2003 and DC power to an AC/DC mixer 2004. A preferred embodiment of the micro-controller 2003 uses an 8 bit 4 MHz micro-controller 2003 but other bit MHz combination micro-controllers may be used. The micro-controller controls AC current flow into an AC/DC mixer 2004. The AC/DC mixer 2004 combines and regulates AC and DC currents that will be used to create a bio-effective magnetic field. A voltage level conversion sub-circuit 2005 controls a transmitted magnetic field delivered to a target treatment site. Output of the voltage level conversion is amplified by an output amplifier 2006 to be delivered as output 2007 that routes a signal to at least one coil 2008. Preferably at least one coil 2008 has a probe 2009 that measures an ambient magnetic field, including geomagnetic components, and sends measurements back to the AC DC mixer 2004 thereby regulating and controlling the configuration of the bio-effective magnetic field. When using ambient magnetic field components to generate a bio-effective magnetic field, a single planar coil may be employed and measurements of the ambient field components used to generate the bio-effective magnetic field can be determined via equation (26). Alternatively to triaxial or biaxial coils in Helmholtz configuration, a single planar coil may be employed, because the magnitude and geometry of the field delivered by such a coil is precisely determined by the input current into the coil and may be calibrated though spatial measurements. For example, a 6-inch diameter applicator coil delivers a resultant magnetic field with x, y, and z components that are primarily in the direction perpendicular to the plane of the coil, as illustrated in FIG. 15. Note that, due to the circular symmetry of the system and field cancellation across the axis of the coil, the perpendicular X-Y components yield values close to ambient level (approximately 2 milliGauss) at the center of the coil (FIG. 15, left hand 1501 and middle plots 1502). As shown in FIG. 15, right hand plot 1503 the dominant component of the magnetic field in the central treatment region is the 2.0 Gauss z-component, perpendicular to the plane of the coil.

EXAMPLES

Example 1

Figure 16:
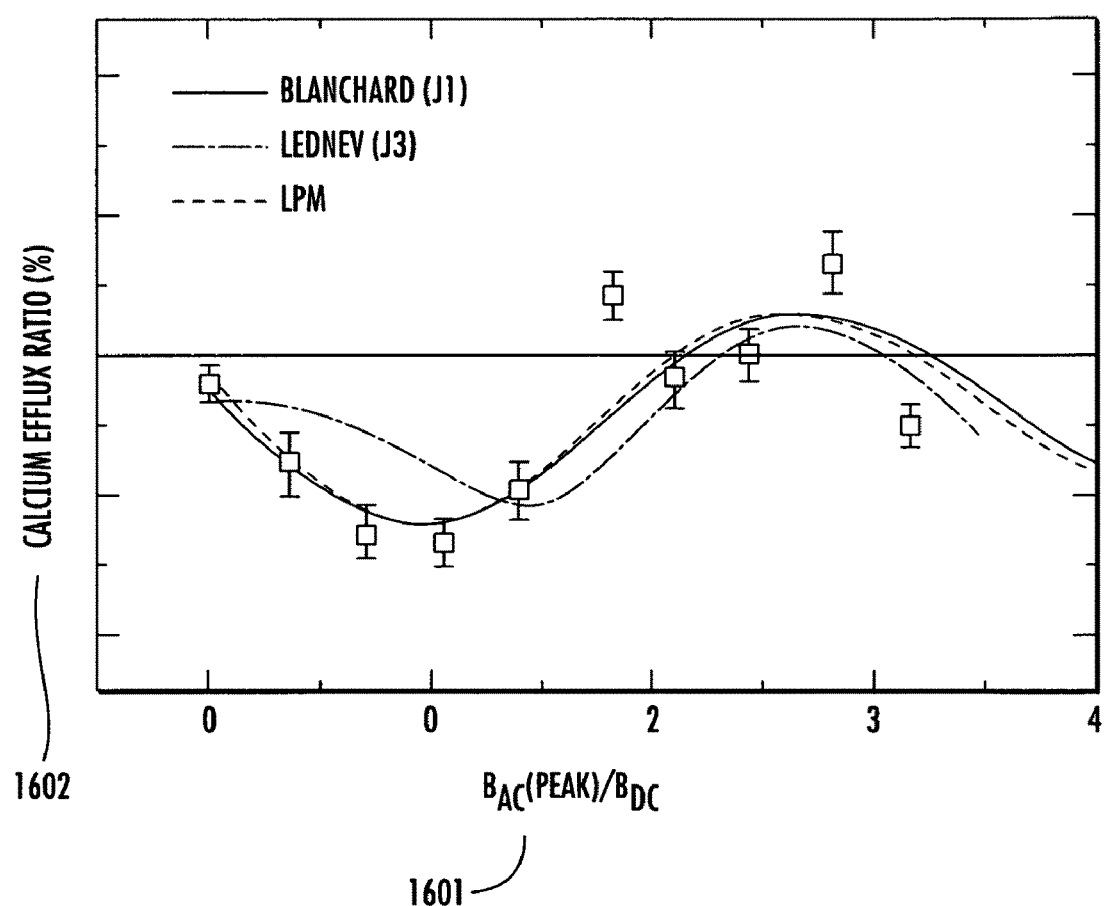
FIG. 16 illustrates predicted LP resonances for an AC/DC parallel magnetic field combination DC=37 µT, AC frequency=24 Hz, taken for 74 msec Larmor period of the 37 µT DC field, as per the method shown in FIGS. 7A, 7B and 7C having applied field frequency plotted on the x-axis 711 and angular displacement plotted on the y-axis 712.

LP explains important experimental results. FIG. 16 having magnetic field combination 1601 plotted on the x-axis and Calcium efflux ration plotted on the y-axis 1602 shows the effect of extremely low frequency magnetic fields on the transport of Ca2⊅ in highly purified plasma membrane vesicles. Vesicles were exposed for 30 min at 32 8 C and the calcium efflux was studied using radioactive $^{45}$Ca as a tracer. Static magnetic fields ranging from 27 to 37 mT and time varying magnetic fields with frequencies between 7 and 72 Hz and amplitudes between 13 and 114 mT (peak) were used. The relative amplitudes of the AC and DC fields are critical in determining the height and position of resonance conditions. Because the Larmor frequency is dependent on the resultant AC+DC amplitude, for AC>DC the oscillator will undergo periodic changes in precessional direction. The resulting resonance conditions may be evaluated for the experimental conditions employed by Koch [Koch, et al., 2003] using equations 17 and 18 with Bperp=0. As may be seen, the LPM fit to the experimental data is essentially identical to that of IPR, but via a more physically realistic mechanism.

Example 2

Figure 17:
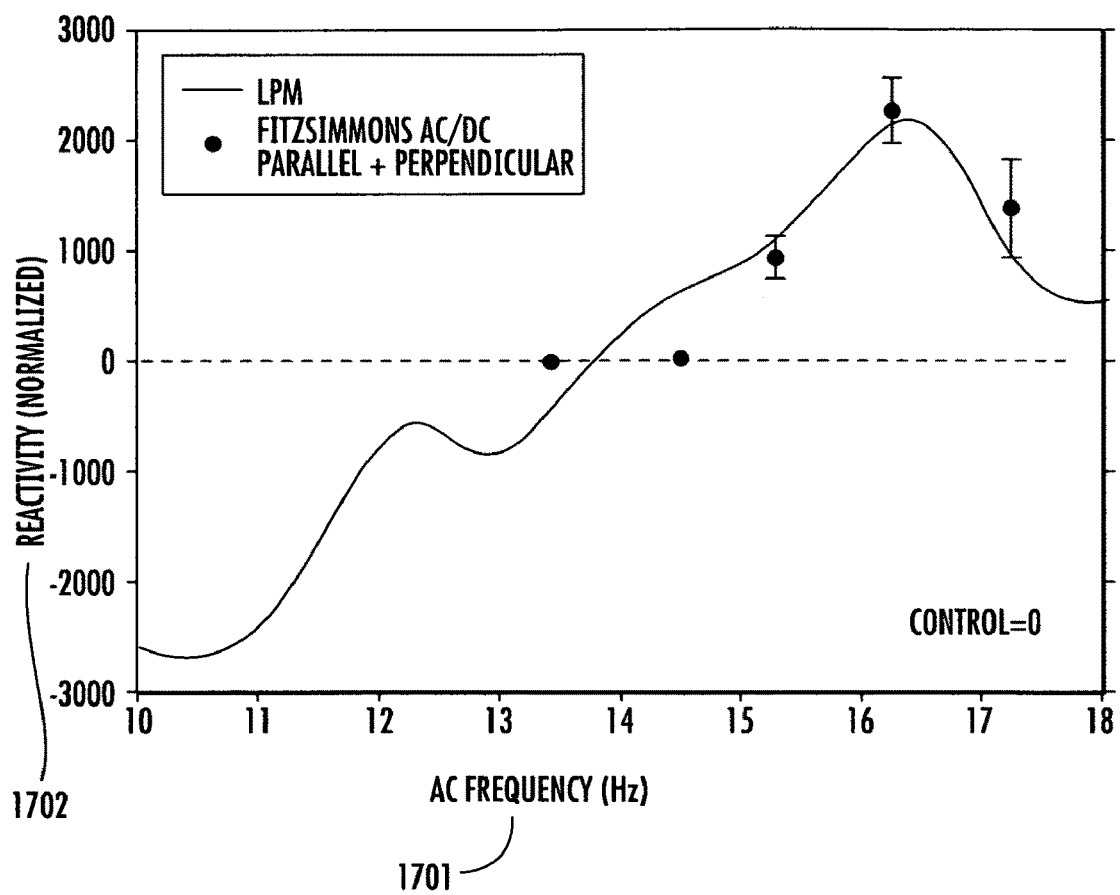
FIG. 17 illustrates predicted LPM resonances for combined Parallel+Perpendicular AC/DC fields, in this case LPM fits the Ca2+ flux data for parallel AC/DC at 20 µT, and 15 µT perpendicular DC reported by Fitzsimmons in 1994 and LPM also predicts inhibition of Ca2+ flux at lower frequencies, not subharmonics of ICR resonance.

FIG. 17 having AC frequency plotted on the x-axis 1701 and reactivity plotted on the y-axis 1702 shows the predictions of LP, via equations 17 and 18, of the results of an experiment measuring Ca flux in bone cells. For this study, net $^{45}$CA flux was used as a possible early marker of the primary transduction response of human bone cells to low-amplitude EMF. The action of a combined DC magnetic field and AC magnetic field were initially configured to couple to calcium binding according to ion cyclotron resonance theory. Although this theory has subsequently been discredited, the experimental results still hold and are successfully explained by LP. The experimental results show a prominent peak in Ca flux in the range of 16 Hz for the applied AC field.

LP predictions for this system, with combined parallel and perpendicular AC/DC fields, for parallel AC/DC at 20 µT combined with 15 µT perpendicular DC, satisfactorily describes the data and also predicts inhibition of Ca2+ flux at lower frequencies that are not sub-harmonics of ICR resonance. These results are clinically relevant for the configuration of bio-effective therapeutic EMF signals.

Example 3

Figure 18:
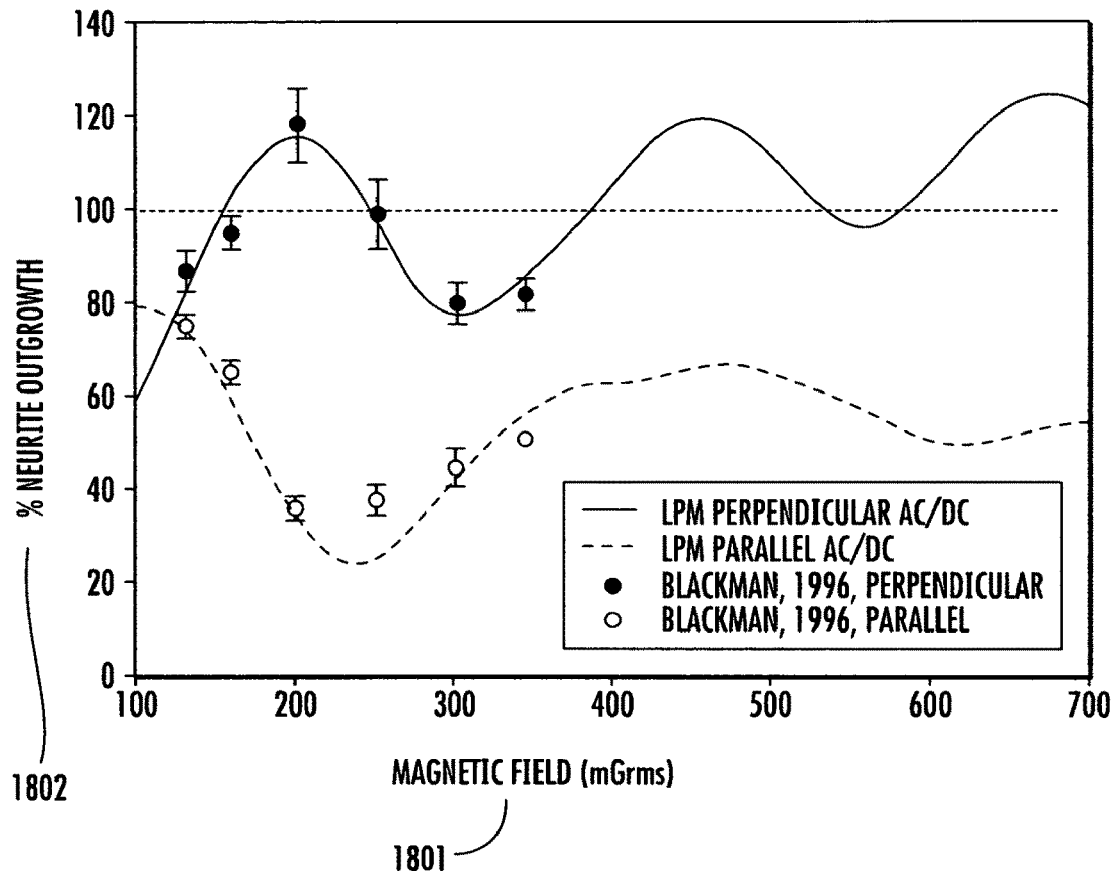
FIG. 18 illustrates predicted LPM resonances for neurite outgrowth from PC-12 cells for 366 mG (36.6 µT) parallel vs. perpendicular field AC/DC combinations with variation in AC amplitude at 45 Hz, as reported by Blackman and LPM accurately fits the data for both parallel and perpendicular orientations and predicts resonance behavior for each orientation at higher AC amplitudes.

FIG. 18 having magnetic field plotted on the x-axis 1801 and Neurite outgrowth on the y-axis 1802 shows LP predictions of amplitude windows for AC magnetic fields. Recent tests of the influence of parallel ac and dc magnetic fields on neurite outgrowth in PC-12 cells showed good agreement with the predictions of an ion parametric resonance model. However, experimental results from earlier work involving both a perpendicular (160 mG) and a parallel (366 mG) dc magnetic field were not as consistent with the ion parametric resonance model predictions. Test results reported here show that the cell response to perpendicular ac and dc magnetic fields is distinct and predictably different from that found for parallel ac and dc magnetic fields, and that the response to perpendicular fields is dominant in an intensity dependent nonlinear manner.

FIG. 18 shows LP predictions of amplitude windows for AC magnetic fields as compared with experimental results obtained by Blackman, for the substantially different effects of AC perpendicular or parallel to a DC magnetic field on neurite outgrowth from PC-12 cells in culture. LP predictions are made via equations 17 and 18 wherein R(t) is evaluated for 75 msec, the Larmor period of the 366 mG DC field. Experimental conditions were 366 mG (36.6 µT) parallel vs perpendicular field AC/DC combinations, along with variation of AC amplitude at 45 Hz. As may be seen, LP satisfactorily describes the results obtained with both perpendicular and parallel field geometry. This observed change in reactivity for parallel vs. perpendicular field orientations is an inherent feature of LP, not explained by any other models.

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

What is claimed is:

1. An electromagnetic apparatus comprising:
   a magnetic field configuration means for configuring a magnetic field by using a Larmor Precession mathematical model to determine a bio-effective magnetic field configuration;
   a power supply for supplying power to the electromagnetic apparatus;
   a mixer for superposing spatiotemporal magnetic field components into the bio-effective magnetic field configuration;
   a measuring device for identifying and measuring components of an ambient magnetic field and sending measurements to the mixer thereby regulating and controlling the configuration of the bio-effective magnetic field;
   a coupling device for generating a bio-effective magnetic field directed to a treatment site, from the bio-effective magnetic field configuration that satisfies the Larmor Precession mathematical model.

2. The electromagnetic apparatus of claim 1, wherein the treatment is adapted to be focused on a site that includes at least one of tissues, cells, organs and molecules.

3. The electromagnetic apparatus of claim 1, wherein the ambient magnetic field includes a geomagnetic field.

4. The electromagnetic apparatus of claim 1, wherein the mixer includes a mixer that can configure a bio-effective magnetic field having at least one of an AC/DC parallel field configuration, an AC/DC perpendicular field configuration, and an AC/DC arbitrary field configuration.

5. The electromagnetic apparatus of claim 1, wherein the mixer includes a mixer that can configure a bio-effective magnetic field having a DC magnetic field having amplitude of about 0.01 G to 5,000 G.

6. The electromagnetic apparatus of claim 1, wherein the mixer includes a mixer that can configure a bio-effective magnetic field having at least one of a DC and AC magnetic field having amplitude of about 0.01 G to 5,000 G in superposition with at least one of an AC and DC magnetic field having an amplitude of about 0.01 G to 5,000 G and frequency from about 0.01 Hz to 36 MHz.

7. The electromagnetic apparatus of claim 1, wherein the mixer includes a mixer that can configure a bio-effective magnetic field having at least one of a DC and AC magnetic field having amplitude of about 0.01 G to 5,000 G in superposition with at least one of an AC and DC magnetic field having an amplitude of about 0.01 G to 5,000 G and frequency from about 0.01 Hz to 36 MHz to enhance biochemical processes in tissues, organs, cells and molecules.

8. The electromagnetic apparatus of claim 1, wherein the mixer includes a mixer that can configure a bio-effective magnetic field having at least one of a DC and AC magnetic field having amplitude of about 0.01 G to 5,000 G in superposition with at least one of an AC and DC magnetic field having an amplitude of about 0.01 G to 5,000 G and frequency from about 0.01 Hz to 36 MHz to inhibit biochemical processes in tissues, organs, cells and molecules.

9. The electromagnetic apparatus of claim 1, wherein the mixer includes a mixer that can configure a bio-effective magnetic field comprising superposition of a signal satisfying Larmor Precession conditions, the signal having a bipolar pulse train, yielding a signal of variable waveform, with amplitude from about 0.01 G to 5,000 G.

10. The electromagnetic apparatus of claim 1, wherein the mixer includes a mixer that can configure a bio-effective magnetic field comprising superposition of a signal satisfying Larmor Precession conditions, the signal having a bipolar pulse train, yielding a signal of variable waveform, with amplitude from about 0.01 G to 5,000 G to enhance biochemical processes in tissues, organs, cells and molecules.

11. The electromagnetic apparatus of claim 1, wherein the mixer includes a mixer that can configure a bio-effective magnetic field comprising superposition of a signal satisfying Larmor Precession conditions, the signal having a bipolar pulse train, yielding a signal of variable waveform, with amplitude from about 0.01 G to 5,000 G to inhibit biochemical processes in tissues, organs, cells and molecules.

12. The electromagnetic apparatus of claim 1, wherein the coupling device comprises at least one electrical coil which transmits the AC/DC signal to the biological target.

13. The electromagnetic apparatus of claim 1, wherein the coupling device comprises at least one of a biaxial and a triaxial configuration of Helmholtz coils.

14. An electromagnetic apparatus configured to provide a bio-effective magnetic field according to a Larmor Precession model, the apparatus comprising:
   a controller for configuring a magnetic field according to a Larmor Precession model to determine a bio-effective magnetic field configuration;
   a power supply for supplying power to the electromagnetic apparatus;
   a mixer for superposing spatiotemporal magnetic field components into the bio-effective magnetic field configuration;
   a measuring device for identifying and measuring components of an ambient magnetic field and sending measurements to the mixer thereby regulating and controlling the configuration of the bio-effective magnetic field;
   a coupling device for generating a bio-effective magnetic field directed to a treatment site, wherein the bio-effective magnetic field is configured by the controller.

15. An electromagnetic apparatus configured to provide a bio-effective magnetic field according to a Larmor Precession model, the apparatus comprising:
   a controller for configuring a magnetic field to a bio-effective magnetic field configuration that satisfies the Larmor Precession model;
   a power supply for supplying power to the electromagnetic apparatus;

a mixer for superposing spatiotemporal magnetic field components into the bio-effective magnetic field configuration;

a measuring device for identifying and measuring components of an ambient magnetic field and sending measurements to the mixer for regulation and control of the configuration of the bio-effective magnetic field;

a coil for generating a bio-effective magnetic field directed to a treatment site, wherein the generated bio-effective magnetic field is configured by the controller to satisfy the Larmor Precession model.

16. The electromagnetic apparatus of claim 15, wherein the coil is adapted to be focused on a site that includes at least one of tissues, cells, organs and molecules.

17. The electromagnetic apparatus of claim 15, wherein the ambient magnetic field includes a geomagnetic field.

18. The electromagnetic apparatus of claim 15, wherein the mixer includes a mixer that can configure a bio-effective magnetic field having at least one of an AC/DC parallel field configuration, an AC/DC perpendicular field configuration, and an AC/DC arbitrary field configuration.

19. The electromagnetic apparatus of claim 15, wherein the mixer includes a mixer that can configure a bio-effective magnetic field having a DC magnetic field having amplitude of about 0.01 G to 5,000 G.

20. The electromagnetic apparatus of claim 15, wherein the mixer includes a mixer that can configure a bio-effective magnetic field having at least one of a DC and AC magnetic field having amplitude of about 0.01 G to 5,000 G in superposition with at least one of an AC and DC magnetic field having an amplitude of about 0.01 G to 5,000 G and frequency from about 0.01 Hz to 36 MHz.

21. The electromagnetic apparatus of claim 15, wherein the mixer includes a mixer that can configure a bio-effective magnetic field comprising superposition of a signal satisfying Larmor Precession conditions, the signal having a bipolar pulse train of known characteristics, yielding a signal of variable waveform, with amplitude from about 0.01 G to 5,000 G.

22. The electromagnetic apparatus of claim 15, wherein the coupling device comprises at least one of a biaxial and a triaxial configuration of Helmholtz coils.

* * * * *